US008206389B2

(12) United States Patent
Huebner et al.

(10) Patent No.: US 8,206,389 B2
(45) Date of Patent: Jun. 26, 2012

(54) ROD-BASED SYSTEM FOR BONE FIXATION

(76) Inventors: Randall J. Huebner, Beaverton, OR (US); Shawn W. O'Driscoll, Rochester, MN (US); Bryon M. Morse, Milwaukie, OR (US); Steven P. Horst, Dayton, OR (US)

(*) Notice: Subject to any disclaimer, the term of this patent is extended or adjusted under 35 U.S.C. 154(b) by 615 days.

(21) Appl. No.: 11/897,760

(22) Filed: Aug. 31, 2007

(65) Prior Publication Data

US 2009/0062797 A1    Mar. 5, 2009

(51) Int. Cl.
  *A61B 17/56* (2006.01)
(52) U.S. Cl. ............................................. 606/62; 606/96
(58) Field of Classification Search .............. 606/62–68, 606/96–99
  See application file for complete search history.

(56) References Cited

U.S. PATENT DOCUMENTS

| | | | |
|---|---|---|---|
| 2,077,804 A | | 4/1937 | Morrison |
| 2,381,050 A | | 8/1945 | Hardinge |
| 2,397,545 A | | 4/1946 | Hardinge |
| 2,614,559 A | | 10/1952 | Livingston |
| 2,696,817 A | | 12/1954 | Prevo |
| 2,821,979 A | | 2/1958 | Cameron |
| 2,952,254 A | | 9/1960 | Keating |
| 3,118,444 A | | 1/1964 | Serrato, Jr. |
| 3,763,855 A | * | 10/1973 | McAtee .................. 606/64 |
| 3,990,438 A | | 11/1976 | Pritchard |
| 4,080,666 A | * | 3/1978 | Fixel ............... 623/23.26 |
| 4,212,294 A | * | 7/1980 | Murphy ................. 606/64 |
| 4,281,649 A | * | 8/1981 | Derweduwen ............ 606/64 |
| D268,870 S | | 5/1983 | Dohogne |
| 4,574,795 A | | 3/1986 | Georges |
| 4,590,930 A | | 5/1986 | Kurth et al. |
| 4,622,959 A | | 11/1986 | Marcus |
| 4,697,585 A | | 10/1987 | Williams |
| 4,791,919 A | | 12/1988 | Elloy et al. |
| 4,858,601 A | | 8/1989 | Glisson |
| 4,913,137 A | | 4/1990 | Azer et al. |
| 4,997,433 A | | 3/1991 | Goble et al. |
| 5,013,314 A | | 5/1991 | Firica et al. |
| 5,013,316 A | | 5/1991 | Goble et al. |
| 5,053,035 A | | 10/1991 | McLaren |

(Continued)

OTHER PUBLICATIONS

Copenheaver, Blaine R., Authorized officer, International Searching Authority, International Search Report, International Patent Application Serial No. PCT/US2008/074799; search date: Oct. 10, 2008.

(Continued)

*Primary Examiner* — Eduardo C Robert
*Assistant Examiner* — Lynnsy Schneider
(74) *Attorney, Agent, or Firm* — Kolisch Hartwell, PC

(57) ABSTRACT

A method of bone fixation. A guide device may be disposed such that a first portion of the guide device is disposed longitudinally in a medullary canal of a bone and such that a second portion of the guide device is disposed outside the bone and defines a transverse path across the bone and intersecting the medullary canal. A transverse hole may be formed in the bone along the transverse path, and a fastener may be disposed in the transverse hole. A rod may be placed longitudinally in the medullary canal such that a threaded portion of the rod enters an aperture of the fastener and engages the fastener at the aperture to lock the rod to the fastener. The first portion of the guide device may be removed from the medullary canal after the step of forming a transverse hole and before the step of placing a rod.

10 Claims, 10 Drawing Sheets

U.S. PATENT DOCUMENTS

| | | |
|---|---|---|
| 5,057,110 A | 10/1991 | Kranz et al. |
| 5,100,405 A | 3/1992 | McLaren |
| 5,108,398 A | 4/1992 | McQueen et al. |
| 5,201,735 A * | 4/1993 | Chapman et al. ............... 606/67 |
| 5,281,224 A | 1/1994 | Faccioli et al. |
| 5,312,406 A | 5/1994 | Brumfield |
| 5,443,466 A * | 8/1995 | Shah ............................... 606/62 |
| 5,472,444 A | 12/1995 | Huebner et al. |
| 5,549,609 A | 8/1996 | Frankel et al. |
| 5,643,258 A | 7/1997 | Robioneck et al. |
| 5,658,288 A | 8/1997 | Kim |
| 5,665,086 A | 9/1997 | Itoman et al. |
| 5,665,087 A | 9/1997 | Huebner |
| 5,743,908 A | 4/1998 | Kim |
| 5,766,174 A * | 6/1998 | Perry .............................. 606/62 |
| 5,779,704 A | 7/1998 | Kim |
| 5,899,906 A | 5/1999 | Schenk |
| 5,997,541 A | 12/1999 | Schenk |
| 6,039,739 A | 3/2000 | Simon |
| 6,048,344 A * | 4/2000 | Schenk ......................... 606/916 |
| 6,080,159 A | 6/2000 | Vichard |
| 6,221,074 B1 | 4/2001 | Cole et al. |
| 6,379,360 B1 * | 4/2002 | Ackeret et al. ................. 606/67 |
| 6,402,753 B1 | 6/2002 | Cole et al. |
| 6,494,913 B1 | 12/2002 | Huebner |
| 6,517,541 B1 | 2/2003 | Sesic |
| 6,660,009 B1 | 12/2003 | Azar |
| 6,730,090 B2 | 5/2004 | Orbay et al. |
| 6,778,861 B1 | 8/2004 | Liebrecht et al. |
| 7,018,380 B2 | 3/2006 | Cole |
| 7,041,104 B1 | 5/2006 | Cole et al. |
| 2002/0151897 A1 | 10/2002 | Zirkle, Jr. |
| 2004/0122428 A1 * | 6/2004 | Johnstone ....................... 606/62 |
| 2004/0193175 A1 * | 9/2004 | Maroney et al. .............. 606/102 |
| 2005/0027294 A1 | 2/2005 | Woll |
| 2006/0161155 A1 | 7/2006 | Schlienger et al. |
| 2007/0100342 A1 * | 5/2007 | Green et al. .................... 606/64 |

OTHER PUBLICATIONS

Copenheaver, Blaine R., Authorized officer, International Searching Authority, Written Opinion of the International Searching Authority, International Patent Application Serial No. PCT/US2008/074799; completion of opinion date: Oct. 29, 2008.

U.K. Intellectual Property Office, Patents Act 1977: Examination Report under Section 18(3), U.K. Patent Application No. 1005451.8; dated Jan. 24, 2012.

* cited by examiner

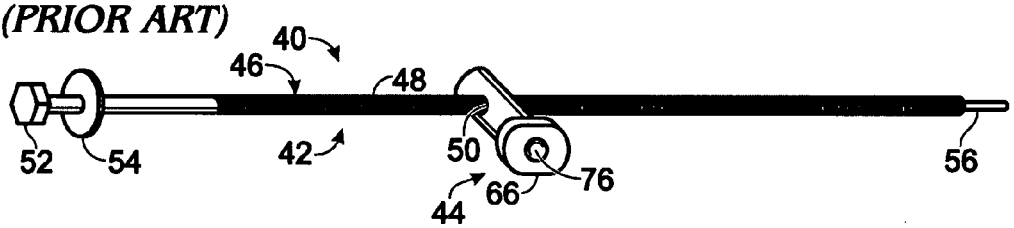
Fig. 1
(PRIOR ART)
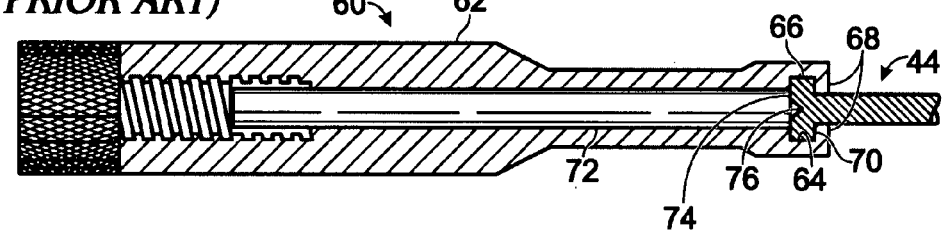
Fig. 2
(PRIOR ART)
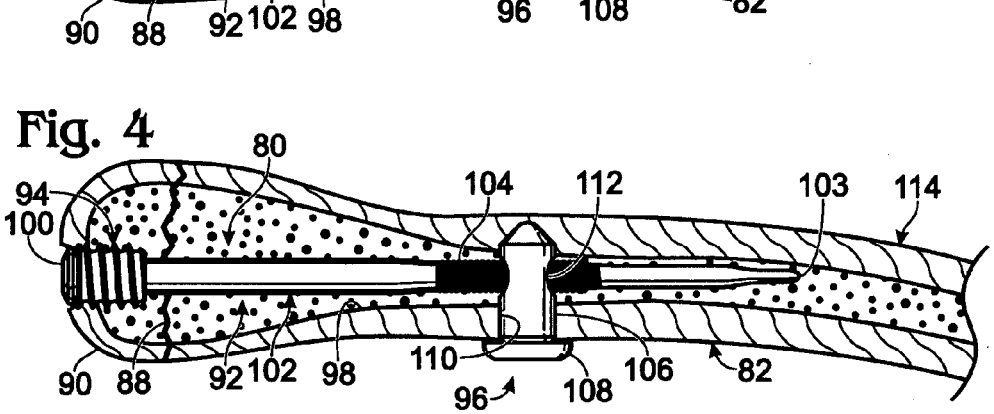
Fig. 3
Fig. 4

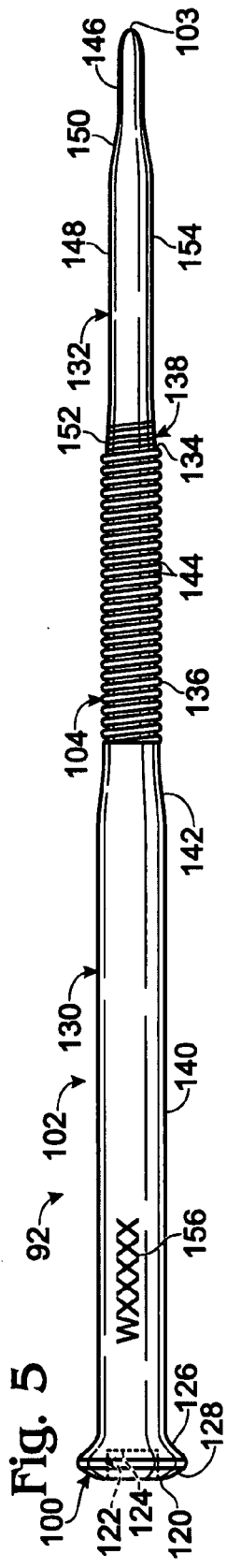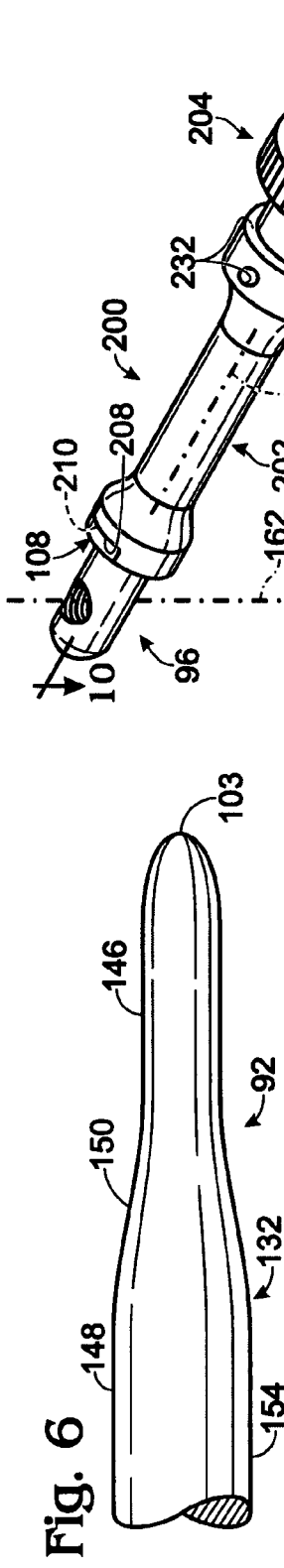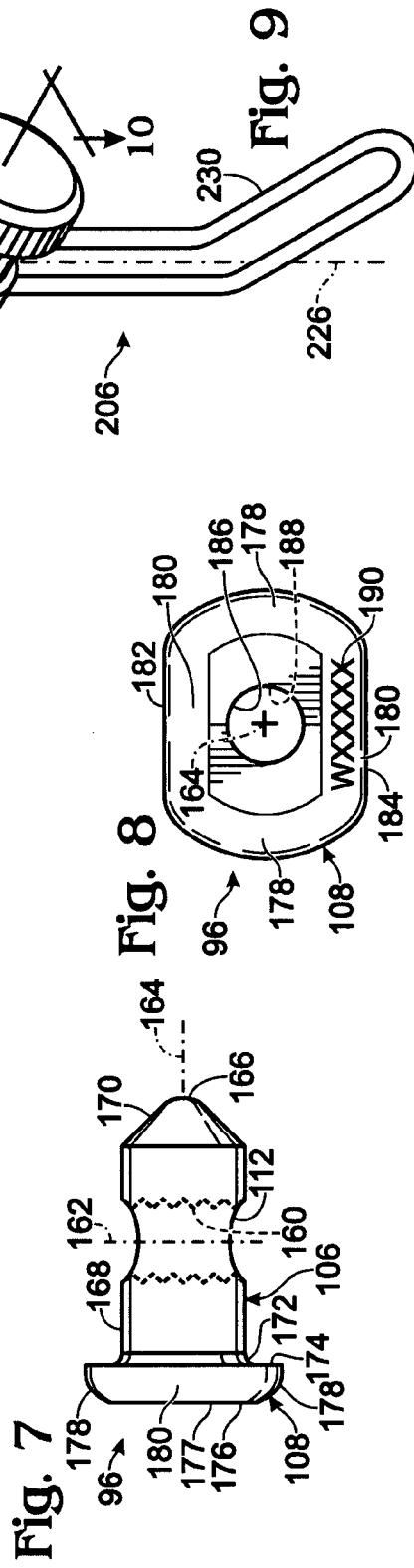

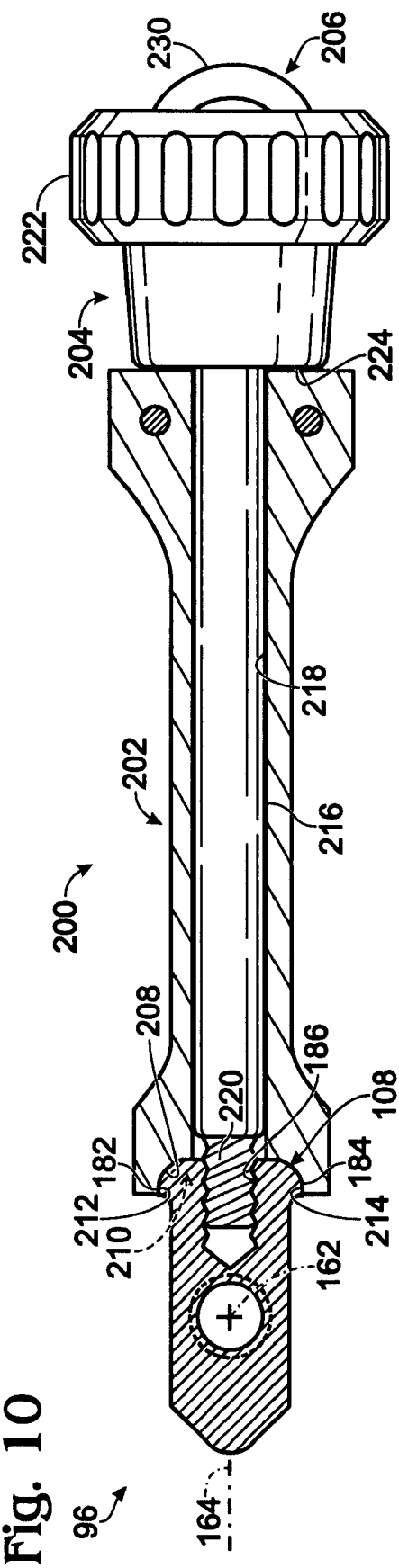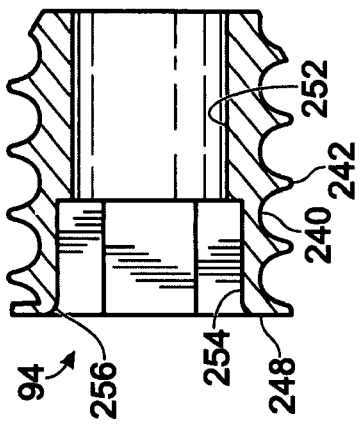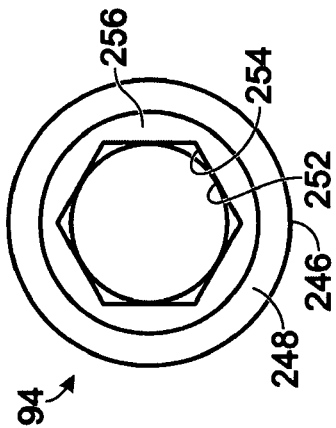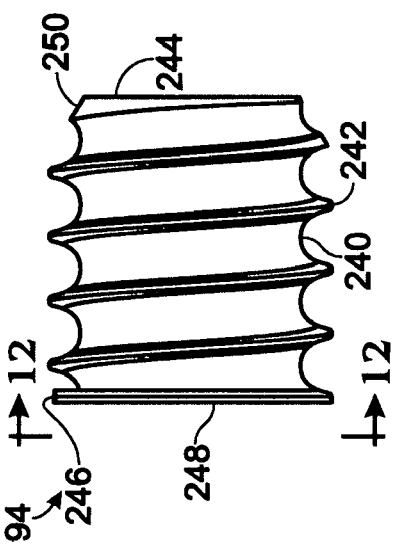

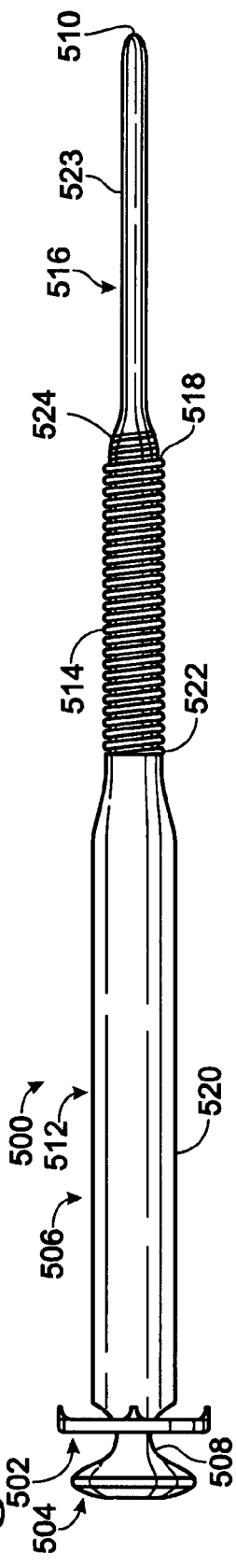
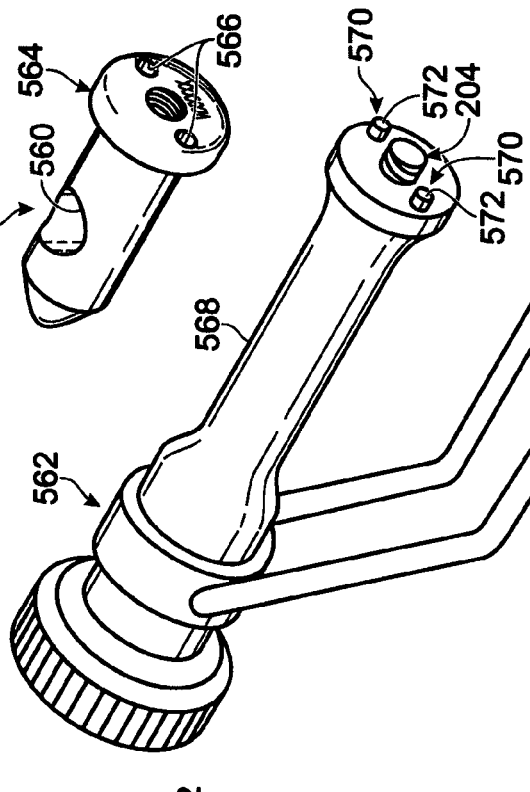
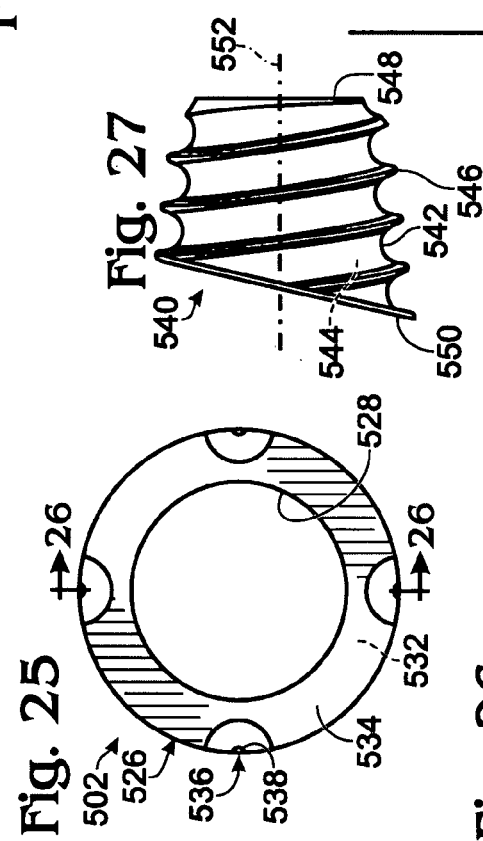
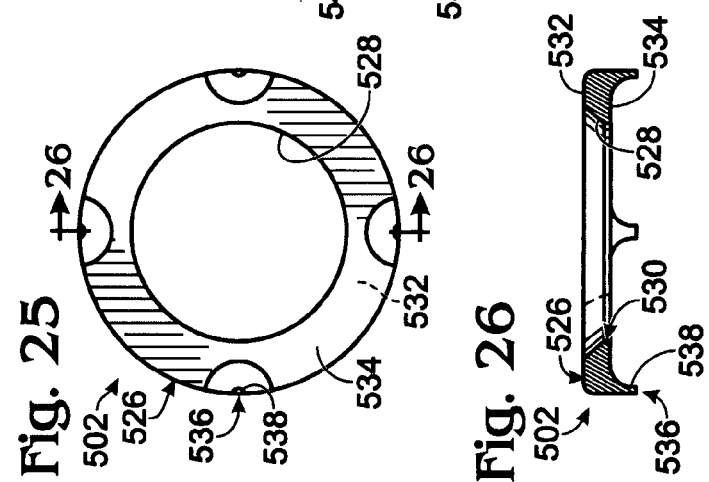
Fig. 24
Fig. 25
Fig. 26
Fig. 27
Fig. 28

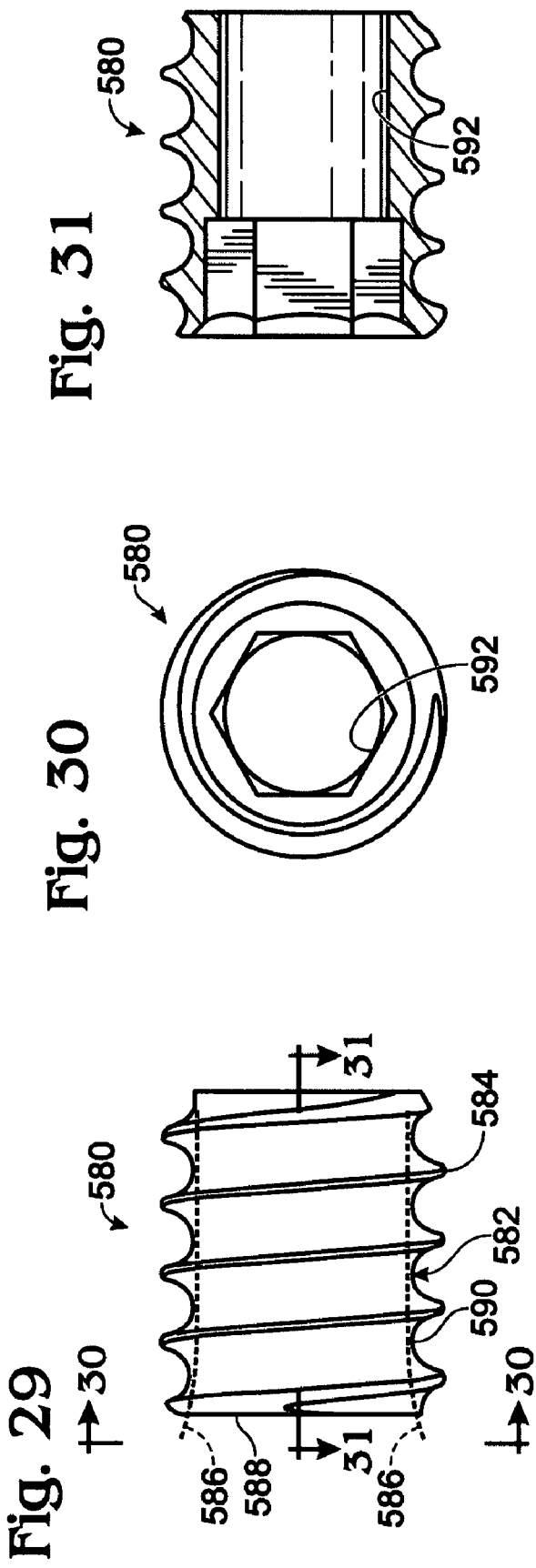

ROD-BASED SYSTEM FOR BONE FIXATION

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, a fractured bone is treated using a fixation device, which reinforces the fractured bone and keeps it aligned during healing. Fixation devices may take a variety of forms, including casts and fixators for external fixation, and bone plates, rods, and bone screws for internal fixation, among others.

Intramedullary rods/nails may function as fixation devices that are received longitudinally in the medullary canal of a broken and/or cut bone. For installation of an intramedullary rod, the medullary canal may be accessed from an end and/or side of the bone with an instrument such as an awl or saw. The medullary canal also may be prepared to receive the intramedullary rod by forming a longitudinal hole in the canal and/or by enlarging the canal. After intramedullary rod placement into the medullary canal, the rod may be secured in position using fasteners, for example, by attaching the rod to two or more bone fragments disposed on opposing sides of a break or cut in the bone. The intramedullary rod thus may include a plurality of transverse apertures that receive threaded fasteners, such as bone screws, which may be anchored in bone adjacent each aperture via an external thread. However, intramedullary rods with transverse apertures generally do not provide a straightforward mechanism for adjusting longitudinal compression of the bone. Accordingly, bone fragments fixed with an intramedullary rod may not be juxtaposed sufficiently for proper healing.

FIG. 1 shows a fixation device 40 that provides a distinct approach to supporting a bone by device placement in the medullary canal, as disclosed by U.S. Pat. No. 3,763,855 to McAtee ("the '855 patent"), which is incorporated herein by reference. Device 40 is disclosed to be suitable for fixation of ulna fractures, particularly in the olecranon region (the elbow protuberance) of the ulna. The device includes a fixation pin 42 for placement longitudinally into the medullary canal of the ulna from the proximal end thereof (i.e., through the elbow protuberance of the ulna). The device also includes a cortical fixation unit 44 for placement transversely into the ulna and medullary canal at a position intermediate the opposing ends of the ulna. Fixation pin 42 provides a slender, flexible body 46 with an external thread 48 extending along a majority of the length of the body. Cortical fixation unit 44 defines an internally threaded aperture 50 that threadably receives external thread 48 to lock fixation pin 42 to fixation unit 44. Fixation pin 42 also includes a head 52 to restrict advancement of the fixation pin into bone. In particular, fixation device 40 is disclosed to include a washer 54 slidably received on body 46 such that, as the fixation pin is advanced to its fully installed configuration, the washer engages a proximal end of the ulna and provides a bearing surface for head 52. The fixation pin also has a tip 56 to facilitate placement of the fixation pin into aperture 50 of cortical fixation unit 44.

FIG. 2 shows a holder 60 from the '855 patent for holding cortical fixation unit 44 during installation of fixation device 40. Holder 60 has a body 62 that defines a channel 64 for receiving a head 66 of the cortical fixation unit. In particular, body 62 includes a pair of opposing fingers 68 that extend to an underside 70 of head 66 to restrict longitudinal movement of the cortical fixation unit. Lateral movement of the cortical fixation unit is restricted by a retainer shaft 72 that is urged against outer surface 74 of head 66, such that a pointed end of the retainer shaft enters a recess 76 of head 66 of the cortical fixation unit.

The fixation device disclosed by the '855 patent may have some advantages over standard intramedullary rods/nails that define apertures for receiving fasteners. For example, the external thread extending along most of the length of fixation pin 42 allows a practitioner to place cortical fixation unit 44 crosswise into the ulna over a broad range of permitted positions along the ulna, to accommodate fractures disposed at different positions along the ulna. In addition, because fixation pin 42 is slender, the fixation pin can be driven along the medullary canal without the need for a previously formed hole in the medullary canal to receive the fixation pin. Furthermore, since fixation pin 42 is flexible and because the slender fixation pin can create its own path along the medullary canal, the fixation pin may be advanced along a nonlinear path in the medullary canal, thereby following the medullary canal as the canal bends as it extends along the bone.

However, the potential advantages of the fixation device disclosed by the '855 patent are offset by substantial disadvantages, making the fixation device difficult to install and/or inadequate for stable fixation. For example, placement of fixation pin 42 into aperture 50 of cortical fixation unit 44 inside bone, where tip 56 and aperture 50 are not visible, may be challenging, frustrating, and time-consuming. The difficulty of placement may be exacerbated further by a natural bend in the medullary canal, as the medullary canal extends away from the olecranon region. The bend in the medullary canal tends to flex the linear fixation pin as the pin is advanced along the canal, thus biasing the pin toward a side of the canal and preventing tip 56 from being re-positioned laterally by a practitioner while trying to feed tip 56 into aperture 50 of the fixation unit. Placement of fixation pin 42 into aperture 50 also may be hampered if the cortical fixation unit 44 is not oriented accurately in bone. In this regard, holder 60 of the '855 patent may not provide optimal positioning and manipulation of cortical fixation unit 44. Furthermore, the flexibility of fixation pin 42 may permit unwanted flexion after installation such that the bone is not fixed stably.

SUMMARY

The present disclosure provides systems, including methods, apparatus, kits, and components for rod-based fixation and/or longitudinal compression of bones.

BRIEF DESCRIPTION OF THE DRAWINGS

FIG. 1 is a side view of a prior art fixation device for the olecranon.

FIG. 2 is a partially sectional side view of a prior art holder used to hold a cortical fixation unit of the fixation device of FIG. 1 during installation of the fixation device.

FIG. 3 is a fragmentary view of an ulna and a humerus from a left arm sectioned sagittally, with the ulna including an olecranon fracture and being fixed and compressed longitudinally by an illustrative fixation device, in accordance with aspects of the present disclosure.

FIG. 4 is a view of the fractured ulna and the fixation device of FIG. 3 taken generally along line 4-4 of FIG. 3 through the ulna as a coronal section.

FIG. 5 is a side view of a rod from the fixation device of FIG. 3.

FIG. 6 is a fragmentary side view of the rod of FIG. 5 taken near a leading end of the rod.

FIG. 7 is a side view of a fastener from the fixation device of FIG. 3.

FIG. 8 is an end view of the fastener of FIG. 7 taken from outward of a head of the fastener.

FIG. 9 is a view of the fastener of FIG. 7 mounted on a holder for manipulation of the fastener, in accordance with aspects of the present disclosure.

FIG. 10 is a longitudinal sectional view of the holder and fastener of FIG. 9, taken generally along line 10-10 of FIG. 9.

FIG. 11 is a side view of a collar from the fixation device of FIG. 3.

FIG. 12 is an end view of the collar of FIG. 11, taken generally along line 12-12 of FIG. 11.

FIG. 13 is a longitudinal sectional view of the collar of FIG. 11.

FIG. 24 is a side view of a rod and a collar from another illustrative fixation device, in accordance with aspects of the present disclosure.

FIG. 25 is a view of a leading face of the collar of FIG. 24.

FIG. 26 is a sectional view of the collar of FIG. 24, taken generally along line 26-26 of FIG. 25.

FIG. 27 is a side view of yet another illustrative collar that may be used in a fixation device, in accordance with aspects of the present disclosure.

FIG. 28 is an exploded view of another illustrative fastener and holder that may be included in a system for bone fixation according to aspects of the present disclosure.

FIG. 29 is a side view of still yet another illustrative collar that may be used in a fixation device, in accordance with aspects of the present disclosure.

FIG. 30 is an end view of the collar of FIG. 29, taken generally along line 30-30 of FIG. 29.

FIG. 31 is a longitudinal sectional view of the collar of FIG. 29, taken generally along line 31-31 of FIG. 29.

DETAILED DESCRIPTION

Figure 14:
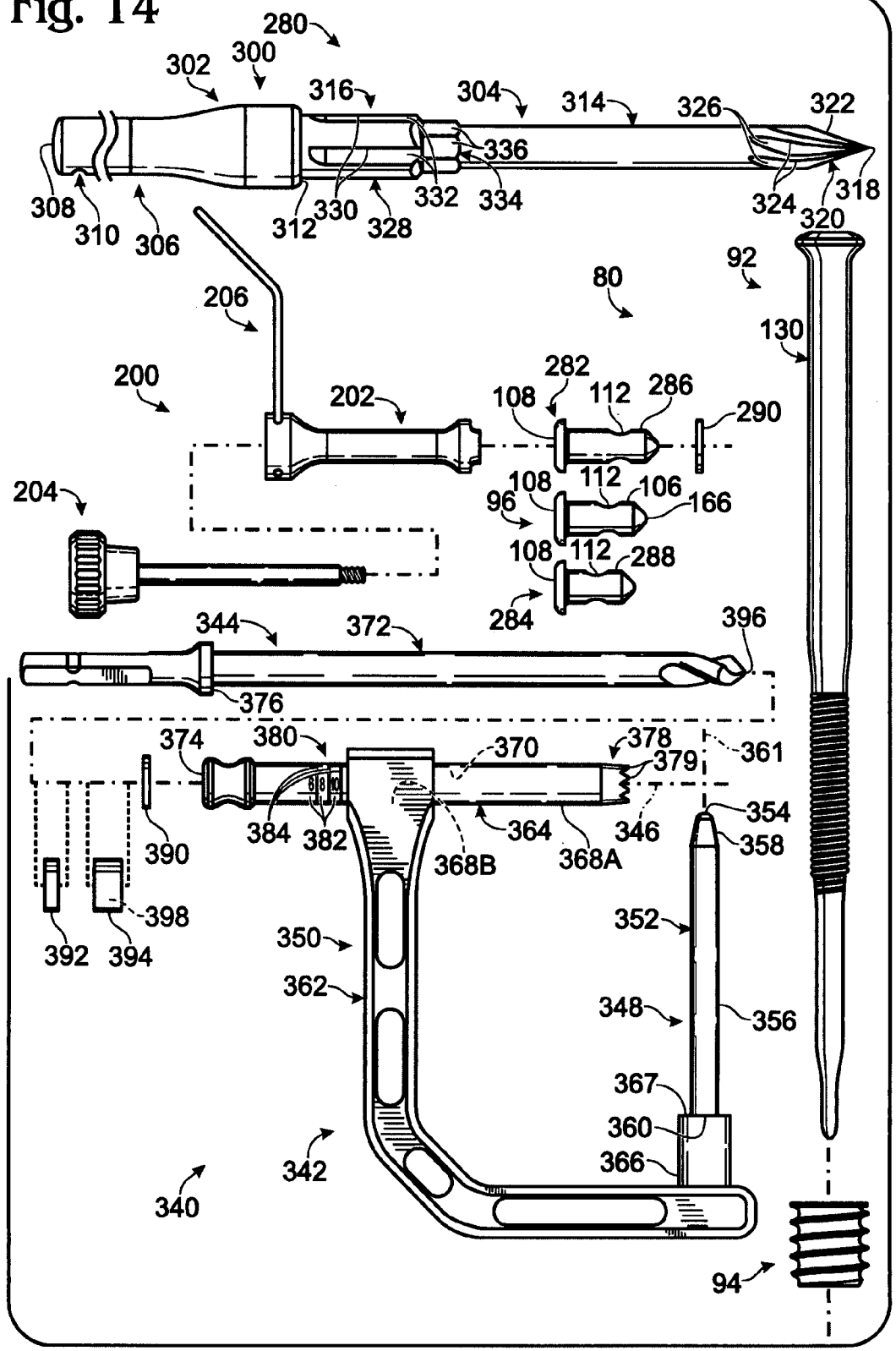
FIG. 14 is a view of selected components of an illustrative system or kit for bone fixation and/or compression that includes the fixation device of FIG. 3, in accordance with aspects of the present disclosure.

The present disclosure provides systems, including methods, apparatus, kits, and components for rod-based fixation and/or longitudinal compression of bones. A system of the present disclosure may include or use a fixation device that includes at least a rod and a fastener. The rod may be for longitudinal placement into a medullary canal of a bone, and the fastener may be for placement into a transverse hole in the bone, with the transverse hole intersecting the medullary canal and particularly intersecting the path along which the rod is placed into bone. The fastener may define an aperture that receives a portion of the rod such that the rod engages the fastener to lock the rod to the fastener (i.e., to restrict relative translational motion of the rod and the fastener). For example, the rod may have an external thread that is disposed in threaded engagement with an internal thread of the aperture of the fastener.

The rod, also termed a nail, may have any suitable features for installation and/or fixation. The rod may include a head and a body extending from the head. The body may include a trailing section with a threaded region for threaded engagement with the fastener. In some examples, the threaded region may extend less than one-half the length of the body. The body and/or the trailing section may be substantially rigid, such that the body and/or trailing section resists flexion, or one or both may be flexible. The body also may include a leading section extending forward of the trailing section and structured to facilitate assembly of the rod with the fastener. For example, the leading section (1) may be much longer than the diameter of a shaft of the fastener, (2) may flare at one or more positions as the leading section extends from a leading end of the rod to the threaded region, (3) may have a length that is at least about one-half the length of the threaded region, and/or (4) may include an elongate tip portion and an elongate intermediate portion disposed between the elongate tip portion and the threaded region and having a greater diameter than the elongate tip portion. In some embodiments, the trailing section of the rod may flare as the trailing section extends from the threaded region to the head, such that a segment of the trailing section is wider than the threaded region. In some embodiments, the head may have an underside that tapers toward the trailing section and/or an outer surface that tapers toward the trailing end of the rod.

The fixation device optionally may include a collar defining an opening through which a body of the rod is received. The collar may be structured to be disposed in and/or on bone and may have one or more projections for engaging bone. For example, the collar may be structured as a sleeve with an external thread, for placement into the end of a bone. In other examples, the collar may have a plate structure (e.g., a washer) for placement onto the end of a bone, with at least one cleat (also termed a prong) that engages bone.

The system optionally may include or use a guide device that couples to the bone to guide formation of the transverse hole in the bone for receiving a fastener. The guide device may couple to the bone via an internal portion, such as a stem, placed into the medullary canal (and/or engaged with the rod). The internal portion may be placed into a pre-formed hole in the medullary canal, which also may receive the rod after removal of the internal portion from the medullary canal, such that the internal portion and the rod occupy overlapping regions of the medullary canal in a mutually exclusive fashion. The internal portion may define a long axis that intersects a transverse path, defined by an external portion of the guide device, for formation of the transverse hole. In some embodiments, the guide device may be configured to measure a radial dimension of the bone. The radial dimension measured may be used to select a depth of the transverse hole to be formed in the bone and/or to select a size of fastener from a set of fasteners of different size for placement into the transverse hole.

The use of a guide device may be enabled by and/or may allow changes in the structure of the rod of the fixation device relative to the prior art. For example, the use of a guide device may guide formation of a transverse hole that provides a substantially predefined position along the rod and bone at which the fastener locks to the rod after installation. Accordingly, in some embodiments, the threaded region of the rod may be shortened relative to the prior art, thereby reducing the number of times the rod must be rotated in threaded engagement with the fastener before the rod is fully installed, and freeing up more of the rest of the rod to have distinct shapes and to perform other functions. The use of a guide device also may provide precise alignment between the rod and the aperture of the fastener. The predefined position at which the guide device determines fastener placement may be selected such that the rod, or at least a trailing section of the rod, is disposed in a substantially linear region of the bone, thereby allowing the rod to be installed without bending the rod. Accordingly, in some embodiments, the flexibility of the rod may be reduced substantially relative to the prior art, since the precise alignment provided by the guide device may obviate the need for rod flexibility. As a result, a thicker, sturdier, less flexible rod may be used to hold bone fragments in position more effectively.

The system optionally may include or use a holder for manipulation of the fastener during installation of the fixation device. The holder may be graspable and may attach to the fastener such that the holder and the fastener can be manipulated as a unit. The holder may mount the fastener to the holder substantially exclusively via a trailing surface of a head of the fastener such that a leading surface of the head is not engaged, overlapped, and/or obstructed substantially by the holder. Accordingly, the fastener's head can be positioned very near and/or in engagement with bone during installation without interference from the holder and thus while permitting the fastener to be manipulated by the holder. The holder also may include an indicator structure, such as an arm, extending outward, for example, generally radially, from a body of the holder in a direction corresponding to the pivotal orientation of the fastener's aperture. The indicator structure thus may be structured as a handle member that can be grasped by hand and aligned with the bone to ensure that the aperture is oriented properly to receive a leading end of the rod during installation.

The system optionally may include other components for installation of the fixation device. For example, the components may include a hole-forming tool(s) for penetrating the end of the bone, forming a hole along the medullary canal for receiving an internal portion of the guide device and/or the rod, widening an end of the hole to receive the collar, and/or for driving the collar into bone, among others. Alternatively, or in addition, the components may include a drill for use with the guide device to provide a guide assembly for forming the transverse hole in bone. Furthermore, the components may include one or more spacers to adjust the effective length of the fastener(s) and/or to adjust the depth at which the drill forms a transverse hole.

The systems of the present disclosure may provide one or more advantages over other fixation systems that offer longitudinal compression of bone. These advantages may include easier and/or faster installation and/or more stable fixation, among others.

The following sections describe further aspects of the present disclosure, including, among others, (I) an illustrative fixation device, (II) rods, (III) fasteners, (IV) fastener holders, (V) collars, (VI) fixation systems/kits, (VII) methods of fixing and/or compressing bones, (VIII) composition of system components, and (IX) examples.

I. AN ILLUSTRATIVE FIXATION DEVICE

FIGS. 3 and 4 show an illustrative fixation device 80 fixing and longitudinally compressing a fractured ulna 82. In the sagittal sectional view of FIG. 3, a proximal portion of the ulna articulates with a distal end region of a humerus 84 via an elbow joint 86. Ulna 82 has a fracture 88 in an olecranon region 90 (also termed an elbow protuberance) of the proximal ulna.

Fixation device 80 may include a rod (a nail) 92 extending through a collar 94 and disposed in threaded engagement with a transverse fastener 96. The rod may be disposed longitudinally in a medullary canal 98 of ulna 82. Rod 92 may have a head 100 and a body 102 extending from the head to a leading end 103 of the rod. Body 102 may extend through collar 94 and head 100 of the rod may bear against the collar (and/or bone). Body 102 may include a threaded region 104 that engages transverse fastener 96.

Transverse fastener 96 may include a shaft 106 extending from a head 108 (see FIG. 4). Shaft 106 may be received in a transverse hole 110 formed in the ulna such that head 108 is disposed close to and/or abuts the exterior surface of the ulna. Shaft 106 may define a transverse aperture 112 having an internal thread for threaded engagement with threaded region 104 of rod 92. Accordingly, in order to provide threaded engagement with the rod, transverse hole 110 of the ulna should have an orientation and depth that position transverse aperture 112 concentrically with respect to the long axis of the rod and thus threaded region 104 of the rod. As described in more detail below, the systems of the present disclosure may guide proper formation of the transverse hole. For example, the systems may guide formation of the transverse hole within a predefined, substantially linear end portion of a bone extending from the end of the bone. Accordingly, the transverse hole may be formed before the bone and medullary canal bend significantly, as indicated at 114 for the natural bend of about ten to fifteen degrees present in the human ulna.

II. RODS

Rods (also termed nails) for fixation devices of the present disclosure may have any suitable size, shape, and features. Aspects of rods that may be suitable are described in this section, in the context of rod 92 of fixation device 80 (e.g., see FIGS. 3 and 4), and below in Example IX, among others.

FIGS. 5 and 6 show a full-length (FIG. 5) or fragmentary (FIG. 6) side view of rod 92 from fixation device 80. Rod 92 may include a trailing end 120 opposing leading end 103. Head 100 and body 102 may be disposed between the trailing and leading ends.

Head 100 may be disposed adjacent and/or may provide a trailing end 120. The head may have any suitable shape. For example, the head may include a driver-engagement structure 122 (such as a hexagonal recess 124, a slotted recess, a set of external facets, and/or the like) for advancing the rod with a driver. In some examples, the head may have an underside 126 (also termed an inner surface or leading surface) that tapers (e.g., a linear or a concave/convex curved taper in profile) toward body 102, or the underside may be planar, among others. Alternatively, or in addition, the head may have an outer surface 128 (also termed a trailing surface) that tapers (e.g., a linear or a concave/convex curved taper in profile) toward trailing end 120. In some examples, at least a portion (or all) of the outer surface may be substantially planar, as shown here for trailing end 120. The head may have any suitable shape when viewed along the long axis of the rod, such as circular, polygonal (e.g., faceted), elliptical, stellate, rosette, or the like. Furthermore, the head may have a diameter that is less than its characteristic dimension measured along the long axis of the rod (as shown here), to provide a relatively low-profile (or no protrusion) above bone, or may be elongate in a direction parallel to the long axis of the rod.

Body 102 may have any suitable structure. The body may extend generally from head 100 to leading end 103. Accordingly, the body may abut the head or may be separated from the head by, for example, a neck (see Example 1), or may be considered to include the neck. The body may be elongate and linear or bent. Body 102 may include a trailing section 130 and a leading section 132.

Trailing section 130 may extend from head 100 to a forward boundary 134 of threaded region 104 (i.e., to a position at which external thread 136 ends or narrows enough, indicated at 138, that the narrowed thread cannot lock the rod to the transverse fastener. The trailing section may include a tail or butt region 140 that trails threaded region 104. The tail region may be nonthreaded (or threaded with a different external thread than external thread 136) and may be narrower than, about the same diameter as, or wider than the major diameter (the maximum diameter) of threaded region 104. If wider than the threaded region (e.g., as shown here), the trailing section may increase in diameter stepwise as the trailing section extends toward the head from the threaded region, or may have a flared region 142 disposed in tail region 140, such as near a leading end of the tale region and threaded region 104. Flared region 142 may flare at any suitable angle from the long axis of the rod, such as less than about 45, 30, 20 or 10 degrees, among others. The tail region may have any suitable length relative to the threaded region, such as being shorter than, at least about as long as, or longer than the threaded region. Furthermore, the tail region may have any suitable cross-sectional shape, such as circular, elliptical, polygonal, or the like. In some embodiments, the tail region may include a cylindrical portion, which may extend over at least about half or at least most (or all) of the tail region.

Leading section 132 may extend forward from forward boundary 134 to leading end 103. The terms "leading" and "forward," as used herein with respect to a region of an element, mean relatively toward the leading end of the element, and the terms "trailing" and "rearward," as used herein with respect to a region of an element, mean relatively toward the trailing end of the element. The leading section may be sized and shaped to permit translational advancement of the leading section into and/or through the transverse aperture of the transverse fastener. Accordingly, the leading section may have a maximum diameter that is less than the major diameter of threaded region 104 and/or no greater than the diameter of a root portion 144 of threaded region 104 on which external thread 136 is formed. The leading section may be elongate and may have any suitable length. For example, the leading section may be much longer than (1) the distance through the transverse aperture of the transverse fastener (or the diameter of the fastener shaft) or (2) the major diameter of threaded region 104, such as at least about two, three, or four times as long. Alternatively, or in addition, the leading section may be at least about one-half as long, at least about as long as, or longer than the length of threaded region 104.

Leading section 132 may have any suitable changes in diameter as the leading section extends from leading end 103 to forward boundary 134 of the trailing section. For example, leading section 132 may include an elongate tip portion 146 and an intermediate portion 148 (also termed an extension portion or confirmation portion) extending from tip portion 146 to forward boundary 134 of threaded region 104. Tip portion 146 may be generally cylindrical (and/or tapered) and/or may include a cylindrical segment. Intermediate portion 148 may include one or more flared regions 150, 152 disposed rearward of the elongate tip portion. Each flared region may flare at any suitable angle relative to the long axis of the rod, such as less than about 45, 30, 20 or 10 degrees, among others. The leading section may flare immediately rearward of tip portion 146, in flared region 150, then may extend rearward to form a cylindrical segment 154 of intermediate portion 148, which may flare from near its rearward end to form flared region 152. Accordingly, leading section 132 may include at least two distinct portions of distinct diameter, which may be elongate and/or generally cylindrical. Tip portion 146 and extension portion 148 may have any suitable relative lengths. For example, extension portion 148 may be shorter than tip portion 146, at least about the same length as the tip portion, longer than tip portion, or much longer than the tip portion (e.g., at least about one and one-half or two times longer than the tip portion). Leading section 132 may have a uniform cross-sectional shape (e.g., circular, polygonal, elliptical, etc.) or may have a cross-sectional shape that varies (e.g., distinct cross-sectional shapes in tip portion 146 and extension portion 148 of leading section 132).

The rod may have any other suitable features. For example, the rod may define one or more apertures that extend into and/or through the rod. In some embodiments, the rod may be cannulated, with an axial passage extending lengthwise through the rod. In some embodiments, the rod may include an axial passage (e.g., an internally threaded passage) and/or a head structure (e.g., an external thread) for coupling a guide device for transverse hole formation to the rod. In some embodiments, the rod may define one or more crosswise apertures that extend into and/or through the rod. Each crosswise aperture may be locking or nonlocking and thus may include or lack an internal thread. The rod may be configured to extend along any portion or all of the length of a bone, such as less than about one-half, less than about one-fourth, at least about one-fourth, or at least about one-half of the length of the bone, among others. In illustrative embodiments, the rod may have a length of about 2-25, 5-20, 5-15, or 10 centimeters, among others.

The rod may be substantially flexible or inflexible (i.e., substantially rigid). A substantially flexible rod, as used herein, means that the rod can be substantially flexed by hand along at least most of its length. A substantially flexible rod also may flex during placement of the rod along a nonlinear path in a medullary canal. A substantially inflexible rod, as used herein, means that the rod is resistant to flexion by hand along at least most of its length. An inflexible rod may be placed along a linear path in a medullary canal.

In some examples, the rod may be included in a set of rods of different size and/or shape. For example, the rods may be of different length and/or may have threaded regions disposed at distinct positions from the trailing end of the rod. In some embodiments, a suitable rod from the set may be selected according to the position of a bone discontinuity to be fixed relative to the end of the bone (e.g., a longer rod and/or a threaded region disposed farther from the trailing end of the rod for a bone discontinuity disposed farther from the end of the bone to be fixed) and/or according to the type of bone to be fixed, among others. Accordingly, the rod may include indicia 156 corresponding to the length, diameter, head size, thread size, position of the threaded region, and/or the like of the rod.

III. FASTENERS

Fasteners for fixation devices of the present disclosure may have any suitable size, shape, and features. Aspects of fasteners that may be suitable are described in this section, in the context of transverse fastener 96 of fixation device 80 (e.g., see FIGS. 3 and 4), and below in Section IX, among others.

FIG. 7 shows a side view of transverse fastener 96. Fastener 96 may include shaft 106 (also termed a body or stem) extending from head 108. Shaft 106 may define transverse aperture 112 that includes a locking structure for locking the rod to the fastener, such as an internal thread 160 that matches the external thread of the rod. Aperture 112 may define a central axis 162 that is orthogonal or oblique to a central axis 164 of shaft 106 of the fastener. In addition, central axis 162 of the aperture may intersect the central axis of the fastener or may be offset therefrom.

Shaft 106 may have any suitable shape and size. The cross-sectional shape of the shaft may be circular or noncircular (e.g., polygonal, elliptical, rosette, etc.). The shaft generally has a diameter that is greater than the major diameter of the threaded region of the rod with which the transverse fastener is used. The diameter may be uniform along at least a portion of the shaft and/or may vary at one or more positions, for example, tapering toward a leading end 166 of the shaft, along at least a portion or all of the length of the shaft. In some examples, the shaft may include a cylindrical region 168 and a tapered tip region 170 extending forward of the cylindrical region. The tip region may taper toward leading end 166, to provide, for example, a generally conical (including frustoconical) or spherical (including frustospherical) tip region, among others. Alternatively, or in addition, shaft 106 may have a substantially planar leading end to, for example, provide a shaft that is substantially exclusively cylindrical in shape. In some embodiments, the shaft may flare outward, indicated at 172, adjacent head 108. A flared region of the shaft adjacent the head may operate to maintain a slight separation between head 108 and underlying bone when the transverse fastener is inserted into bone. The length of shaft 106 may be selected according to a radial dimension (and/or diameter) of a target bone, for example, such that the distance along the shaft from an underside 174 of head 108 to central axis 162 of aperture 112 is about the same as the distance, at the site of fastener placement, from the exterior surface of the target bone to the central axis of its medullary canal (i.e., the local radial dimension of the target bone). The length of shaft 106 may be selected such that, when installed, shaft 106 and/or cylindrical region 168 spans the medullary canal crosswise.

The shaft may have any suitable surface structure. For example, the shaft may be nonthreaded or may have an external thread. If externally threaded, the external thread may extend along any suitable portion of shaft 106, for example, disposed forward and/or rearward of aperture 112.

Head 108 may have any suitable size and shape. The head may have underside (also termed an inner surface) 174 and outer surface 176 configured to face generally toward and away from bone. Outer surface 176 may include an outer face 177, separated by opposing pairs of side surfaces 178, 180. Inner surface 174 and outer face 177 each may be at least substantially planar, as shown here, or may be nonplanar, for example, a concave (or convex) inner surface and a convex (or concave) outer face, among others. Side surfaces 178, 180 may be planar or nonplanar. For example, the side surfaces may have a beveled or rounded profile, as shown here, to reduce the presence of sharp edges that may damage overlying soft tissue. Inner surface 174 and outer face 177 may be separated by any suitable distance. For example, the inner surface and the outer face may be separated by a distance that is less than the diameter of the head, to provide a relatively thin head (as shown here), or by a distance that is at least about the same as or greater than the diameter of the head to provide a relatively thick head. In addition, outer face 177 and/side surfaces 178, 180 may be separated by one or more distinct boundaries or may transition to one another smoothly.

FIG. 8 shows an end view of fastener 96 taken from outward of head 108. The fastener head may have any suitable shape when viewed along central axis 164. For example, the fastener head may have a perimeter with opposing linear segments 182, 184, to give the fastener a two-fold rotational symmetry. The linear segments may be parallel to central axis 162 of aperture 112 (see FIG. 7) or orthogonal, among others. In other embodiments, head 108 may have any other suitable shape when viewed along central axis 164, such as circular, elliptical, polygonal, etc.

Head 108 may have one or more recesses (and/or projections) for coupling fastener 96 to a holder for installation of fixation device 80. For example, head 108 may define an axial bore 186 having an internal thread 188. The axial bore may be a blind hole or may extend through the fastener lengthwise such that the fastener is cannulated. In some examples, the fastener head may include one or more additional recesses (or projections) for mating with additional projections (or recesses) of the holder (e.g., see Example 3).

Fastener 96 also may include indicia 190 presenting identifying information for the fastener. The indicia may correspond to any suitable aspect(s) of the fastener, such as fastener size, shaft length, shaft diameter, head diameter, head thickness, transverse aperture diameter, transverse aperture thread configuration, composition, and/or the like.

IV. FASTENER HOLDERS

Fixation devices of the present disclosure may be installed using a fastener holder (i.e., a holder device) to advance, position, orient, and provisionally immobilize fasteners of the fixation devices. Aspects of holders that may be suitable are described in this section, in the context of transverse fastener 96 of fixation device 80 (e.g., see FIGS. 3 and 4), and below in Example 3, among others.

FIGS. 9 and 10 show fastener 96 coupled to a holder 200 for manipulation of the fastener during installation of fastener device 80. Holder 200 may include a body portion 202, a securing portion 204, and an orientation indicator 206.

Body portion 202 may be structured to receive and/or engage head 108 of fastener 96. For example, the body portion may have an engagement surface 208 that is complementary to at least a region of outer surface 176 of the head, such as outer face 177 and/or side surfaces 178 and/or 180 (see FIGS. 7 and 8). Engagement surface 208 may define a channel and/or recess 210 into which head 108 may be received. Here, recess 210 has linear side walls 212, 214 that appose linear segments 182, 184 of head 108, such that head 108 is received in a predefined orientation (i.e., in one of two permitted orientations) relative to body portion 202. Furthermore, the body portion may be structured such that holder 200 does not engage, overlap, and/or obstruct inner surface 174 of head 108 (see FIG. 7) during placement of head 108 adjacent bone. Stated differently, body portion 202 and/or holder 200 may not extend axially to a position forward of the head, particularly the inner surface of the head, when the fastener is secured to the holder.

Fastener 96 may be secured to body portion 202 using securing portion 204 of holder 200. In particular, securing portion 204 may include a bar 216 slidably received in a longitudinal bore 218 of body portion 202. Bar 216 may have a threaded tip 220 that is structured and arranged to be threadably received in axial bore 186, in engagement with the internal thread of fastener 96. An opposing end of securing portion 204 may include a handle member 222, such as a knob, which may be knurled or otherwise configured to be grasped manually, for manual adjustment (rotation) of the threaded tip. The opposing end of securing portion 204 also may include a shoulder 224 that bears against the trailing end of body portion 202. Accordingly, the securing portion may be rotated until head 108 of fastener 96 is seated against the body portion of holder 200, and is fixed in position such that relative axial, pivotal, and lateral motion of the fastener is restricted. Central axis 164 of the fastener may be aligned with and/or collinear with the central axis of the body portion. As a result, where fastener 96 is attached to holder 200, the holder may function as a longitudinal (and rearward) extension of fastener 96 as the holder and fastener move as a unit.

Orientation indicator 206 may be structured and arranged to indicate the orientation of central axis 162 of fastener aperture 112. In particular, the orientation indicator may extend along an indicator axis 226 that is generally parallel to central axis 162 of fastener aperture 112, and/or may define an orientation plane, via indicator axis 226 and a central long axis 228 of body portion 202, that includes central axis 162 (see FIG. 9). The orientation indicator may project generally radially from body portion 202 and/or central long axis 228. Accordingly, the orientation indicator may be a handle portion, such as an arm 230, that can be engaged manually (i.e., grasped by hand) to adjust the orientation of fastener 96 by pivoting the fastener about its central axis 164. Arm 230 may be fixed or movable in relation to body portion 202. For example, here, arm 230 includes a bent rod with ends received in openings 232 defined by body portion 202. Arm 230 thus may be secured fixedly to the body portion or may be pivotably coupled to the body portion to allow the arm to be moved to various pivotal positions for storage or use (e.g., see Example 3 for a holder with a pivotable arm disposed in a distinct position).

V. COLLARS

Fixation devices of the present disclosure may include an optional collar. Aspects of collars that may be suitable are described in this section, in the context of collar 94 of fixation device 80 (e.g., see FIGS. 3 and 4), and below in Examples 1, 2, and 4, among others.

FIG. 11 shows a side view of collar 94 from fixation device 80. Collar 94, which also may be described as a sleeve or washer, may include a root portion 240 and an external thread 242 formed on the root portion. The external thread may taper toward a leading end 244 of the collar, to restrict excessive advancement of the collar into bone, or may have a substantially uniform major diameter, as shown here. Advancement of the collar into bone may be restricted by any other suitable mechanism, such as a nonhelical flange 246 (e.g., an annular flange describing a complete or partial circle) formed near a trailing end 248 of the collar, a root portion that is thicker and/or that decreases in depth toward the trailing end of the collar (see Example 4), and/or the like. A leading region 250 of the collar may taper (e.g., may be beveled) to facilitate placement of the collar into a hole in bone.

FIG. 12 is an end view of collar 94. The collar may include an axial channel 252 sized to receive the body of the rod of the fixation device and, optionally, at least a portion or all of the head of the rod. Axial channel 252 may include a driver-engagement structure 254 for driving the collar into bone with a suitable driver. In other embodiments, the driver-engagement structure may be provided by an external surface region(s) of the collar, such as by a series of external facets.

FIG. 13 is a sectional view of collar 94. Axial channel 252 may flare toward trailing end 248 of the collar to form a flared region 256 (also see FIG. 12). The flared region may allow a greater portion (or all) of the head to enter the axial channel and/or may facilitate pivotal motion of the rod's head relative to the collar. In some embodiments, the flared region may define a cavity (such as a frustoconical or frustospherical cavity, among others) that matches the shape of a leading region of the head.

VI. FIXATION SYSTEMS/KITS

The fixation devices of the present disclosure may be included in systems and/or kits with any other suitable components. An illustrative fixation system/kit is described in this section, in the context of fixation device 80 (e.g., see FIGS. 3 and 4).

FIG. 14 shows selected components of an illustrative fixation system 280 that includes fixation device 80 (i.e., rod 92, collar 94, and transverse fastener 96). The system, or any suitable subset thereof, with or without one or more additional components as described elsewhere in the present disclosure, may be provided as a kit for bone fixation and/or longitudinal compression of bone. For example, the kit may include one or more rods (of the same or different size/shape), one or more transverse fasteners (of the same or different size/shape), one or more spacers for the transverse fasteners, one or more collars (of the same or different size/shape/type) for receiving the rod(s), a holder(s) for the transverse fastener(s), a guide device(s), a drill(s), a saw or related cutting tool, a driver(s) for driving the rod/collar/transverse fastener, instructions for use, and/or the like. Some or all of the components of the system/kit may be provided in a sterile condition, such as packaged in a sterile container.

A. Transverse Fasteners

System 280 may include a plurality of transverse fasteners 96, 282, and 284 for assembly with rod 92. The transverse fasteners may have respective shafts 106, 286, and 288 of different lengths. Alternatively, or in addition, the shafts may dispose aperture 112 at distinct distances from head 108 (and/or leading end 166). In illustrative embodiments, for the purposes of illustration, fasteners 96, 282, and 284 may have the central axis of transverse aperture 112 disposed at ten, eight, and six millimeters, respectively, from head 108 (and from the trailing end of each respective shaft). Each transverse fastener may be used with or without at least one spacer element 290. The spacer element may define an opening sized to receive the fastener shaft but not the fastener head, such that the spacer element may be positioned in abutment with the underside of the fastener head. The spacer element thus may be an open or closed annulus or ring, such as a washer. In illustrative embodiments, the spacer element may have a thickness that is less than the difference in length between the transverse fasteners. For example, with the example presented above, in which the shafts differ in length by two millimeters, the spacer element may have a thickness less than two millimeters, such as about one millimeter or 0.5 millimeter, among others.

B. Illustrative Drill

System 280 may include a longitudinal hole-forming tool or drill 300 for placement longitudinally into bone, and may be configured to function as an awl, a reamer, and/or a driver, among others. Tool 300 thus may form a hole in bone for receiving an internal portion of a guide device (see below), rod 92 and/or collar 94 of fixation device 80, and/or may be used to drive collar 94 into bone, among others. Tool 300 may include an elongate shaft 302 structured as a bit to be driven manually via a coupled handle portion and/or crank and/or power-driven by a power driver. Shaft 302 may include an internal portion 304 for introduction into bone and an external portion or extension portion 306 extending from the internal portion to a trailing end 308 of shaft 302.

External portion 306 may be structured to remain outside of bone. The external portion may have an integral handle or may include a coupling structure 310 that is engaged by a fastener mechanism that couples a removable handle or driver to shaft 302. An integral or removable handle may have any suitable disposition relative to the long axis of shaft 302. In some examples, the handle may extend orthogonally or obliquely to the long axis to, for example, provide a generally T-shaped tool. In addition, the external portion may form a stop or shoulder 312 at a boundary between external portion 306 and internal portion 304. Stop 312 may be wider than the maximum diameter of the internal portion, to restrict advancement of the external portion into a hole in bone formed by internal portion 304.

Internal portion 304 may include any suitable structure for forming a hole in bone and/or for installing one or more system components in bone. Forming a hole, also termed drilling, may be performed by any suitable process, including cutting, grinding, and/or compacting, among others. In some examples, the internal portion may include a stem region 314 extending forward of a head region 316 to a leading end 318 of shaft 302. Each of the stem and head regions may include at least one drill region for cutting bone in order to form, widen, and/or shape a hole in bone. For example, stem region 314 may include an awl structure 320 disposed near leading end 318. The awl structure may include a pointed tip 322 and one or more cutting edges 324 created by one or more flutes 326. Stem region 314 may be sized according to rod 92. For example, the stem region may have a diameter that corresponds to a diameter of rod 92 (e.g., about the same diameter as the rod), such as the diameter of a nonthreaded or threaded region of the trailing section of the rod. Alternatively, or in addition, head region 316 may include a reamer structure 328 disposed between external portion 306 and stem region 314. The reamer structure may be configured to widen a hole in bone, such as a hole formed by stem region 314, particularly awl structure 320, and/or by any other suitable mechanism. Reamer structure 328 may include one or more cutting edges 330 created by one or more flutes 332. The reamer structure may be sized to create a hole for receiving collar 94, by widening the hole created by stem region 314. Accordingly, the reamer structure may have a diameter that is about the same as or that corresponds to the minor diameter of the collar, such that an external thread of the collar threadably engages bone when placed in the hole (or so that a nonthreaded collar and/or at least a portion of the rod's head can be placed in the hole). The reamer structure may have any suitable length, such as a length that is about the same as or longer than the length of collar 94, as measured along the central axis through the collar.

Internal portion 304 further may include a driver portion 334 for engagement with a component of fixation device 80, such as collar 94. Accordingly, driver portion 334 may include a plurality of facets 336 for engagement with the driver-engagement structure of the collar. Driver portion 334 thus may include a noncircular cross-section, such as a polygonal cross section. The driver portion may be disposed forward of reamer structure 328, such as between stem region 314 and head region 316. The driver portion may have a diameter that is greater than the diameter of stem region 314 and less than the diameter of the head region 316. Further aspects of tool 300 and its use during installation of fixation device 80 are described below in Section VII.

C. Illustrative Guide Assembly

System 280 further may include a guide assembly 340 for forming a transverse hole in bone for receiving one of transverse fasteners 96, 282, or 284. The guide assembly may include a guide device 342 and a drill 344.

Guide device 342 may be structured to define a guide path or guide axis 346 for hole formation and/or for advancement of drill 344. The guide device may include an internal portion or stem portion 348 for placement longitudinally into bone, such as into a medullary canal having a pre-formed longitudinal hole (e.g., prepared using tool 300). The guide device also may include an external portion 350 connected to the internal portion and extending from the internal portion, and from an end of a bone, to a position that is to the side of the bone.

Internal portion 348 may include a shaft or stem 352 structured to be received in the medullary canal. Stem 352 may have any suitable size and shape. For example, stem 352 may have a diameter corresponding to the diameter of stem region 314 of tool 300, such as a diameter that is about the same as the diameter of stem region 314. Alternatively, or in addition, stem 352 may have a diameter corresponding to a diameter of rod 92, such as a diameter that is about the same as the diameter of the rod's trailing section 130. The diameter of stem 352 may be generally uniform along at least a portion or all of the stem's length or may vary, such as tapering toward a leading end 354 of the stem. Here, stem 352 includes a cylindrical section 356 and a tapered tip section 358. Stem 352 may be elongate and may have any suitable length. For example, the length may be less than or greater than the distance from a trailing end 360 of stem 352 to guide axis 346.

If greater than the distance, stem 352 may define an aperture aligned with guide axis 346 such that drill 344 does not contact stem 352 when drilling is performed. If less than the distance, stem 352 may extend any suitable fraction of the distance, such as less than about one-half the distance, at least about one-half the distance, or most of the distance, among others. In addition, stem 352 may define a central long axis 361 that is orthogonal to and/or intersects guide axis 346 or that is oblique to and/or offset from guide axis 346.

External portion 350 may include a frame 362 and a guide element 364 coupled to the frame. Frame 362 may provide a stop structure 366 adjacent trailing end 360 of stem 352 that restricts entry of external portion 350 into bone via a shoulder 367 of the stop structure. The stop structure thus may have a greater diameter or width than stem 352. The stop structure may be unitary with the body of frame 362 or may be provided by a discrete component that attaches to the frame's body. Furthermore, the position of the stop structure in relation to guide axis 346 may be fixed or adjustable. For example, the stop structure may be adjustably positionable along stem 352, such as with a stop structure configured as an adjustable sleeve that can slide along the stem and then be fixed in position on the stem via a set screw. Alternatively, or in addition, the distance from the stop structure to guide axis 346 may be adjustable via a telescoping frame and/or via interchangeable stop structures (with or without the stems) of different length.

Guide element 364 may have any suitable relationship to frame 362. The guide element may be fixed in relation to frame 362 or may be movable. If movable, the guide element may be movable translationally and/or pivotally, such as movable translationally parallel to guide axis 346 and/or movable pivotally about guide axis 346. If fixed, the guide element may be provided by a discrete component or may be unitary with the frame, such as a channel defined by frame 362.

Guide element 364 may be a sleeve 368A (which may be described as a tube or a cannula) that is slidably or fixedly disposed in an aperture 368B of frame 362. The guide element may define a longitudinal passage 370 sized to receive at least a leading section 372 of drill 344. The guide element may widen externally adjacent a trailing end 374 of the guide element to restrict forward travel of drill 344, such as by engagement with a flange 376 of drill 344. Furthermore, guide element 364 may have a leading end region 378 with one or more projections or serrations 379 for engagement with bone. Accordingly, the leading end region may provide a serrated leading edge.

Guide device 340 also or alternatively may be described as a measuring device. In particular, the guide device may be configured to measure a distance from central long axis 361 of stem 352 to leading end region 378 of guide element 364, which corresponds to a local radial dimension of a bone being measured. The distance may be indicated by indicia or reference marks 380 on guide element 364. Indicia/reference marks 380 may indicate the distance in any suitable form, such as alphanumeric characters 382, other symbols, graduations 384, colors, a combination thereof, and/or the like. In some embodiments, elements of indicia 380 may correspond individually to each of the transverse fasteners, to facilitate selection of an appropriate transverse fastener (and/or to determine whether or not spacer element 290 should be used with the fastener).

Guide assembly 340 also may include one or more spacers 390-394 for adjusting the depth of the transverse hole formed by drill 344. Stated differently, the spacers may adjust the distance that tip 396 of drill 344 can be advanced along guide axis 346 past guide element 364. Each spacer may define a central opening 398 sized to receive leading section 372 of drill 344, but not flange 376 of the drill. Accordingly, in some embodiments, each spacer may be annular, such as a washer. When placed on leading section 372 of drill 344, each spacer may separate flange 376 of drill 344 from trailing end 374 of guide element 364 according to the characteristic dimension (e.g., thickness) of the spacer measured through central opening 398. In other words, each spacer may function to reduce the length of leading section 372 that can be advanced past leading end region 378 of guide element 364, to adjust the depth of the transverse hole in bone formed by drill 344. The characteristic dimension (e.g., thickness) of the spacers may be the same or distinct. For example, here, spacers 390-394 have distinct respective thicknesses of one, two, and four millimeters. Accordingly, the spacers may be used respectively to reduce the depth of the transverse hole formed by drill 344 by one, two, or four millimeters. The spacers may be used in combination, such as spacer 390 combined with spacer 392 to reduce the depth of the transverse hole by three millimeters. In some embodiments, spacer element 290 for the transverse fasteners may be used as spacer 390, or vice versa. In some embodiments, spacers 390-394 may not be needed to adjust the depth of the hole formed by drill 344. For example, the fixation system may adjust the depth of drilling by using drills of different length (e.g., via distinct drill bits used with the same handle/driver), a drill with an adjustable stop, and/or a drill with reference marks disposed along the drill shaft. Alternatively, or in addition, the fixation system may restrict travel of drill 344 by engagement of a stop structure on drill 344 with frame 362, rather than with guide element 364. In this way, the stop structure may have a fixed distance from central long axis 361 of stem 352.

Figure 15:
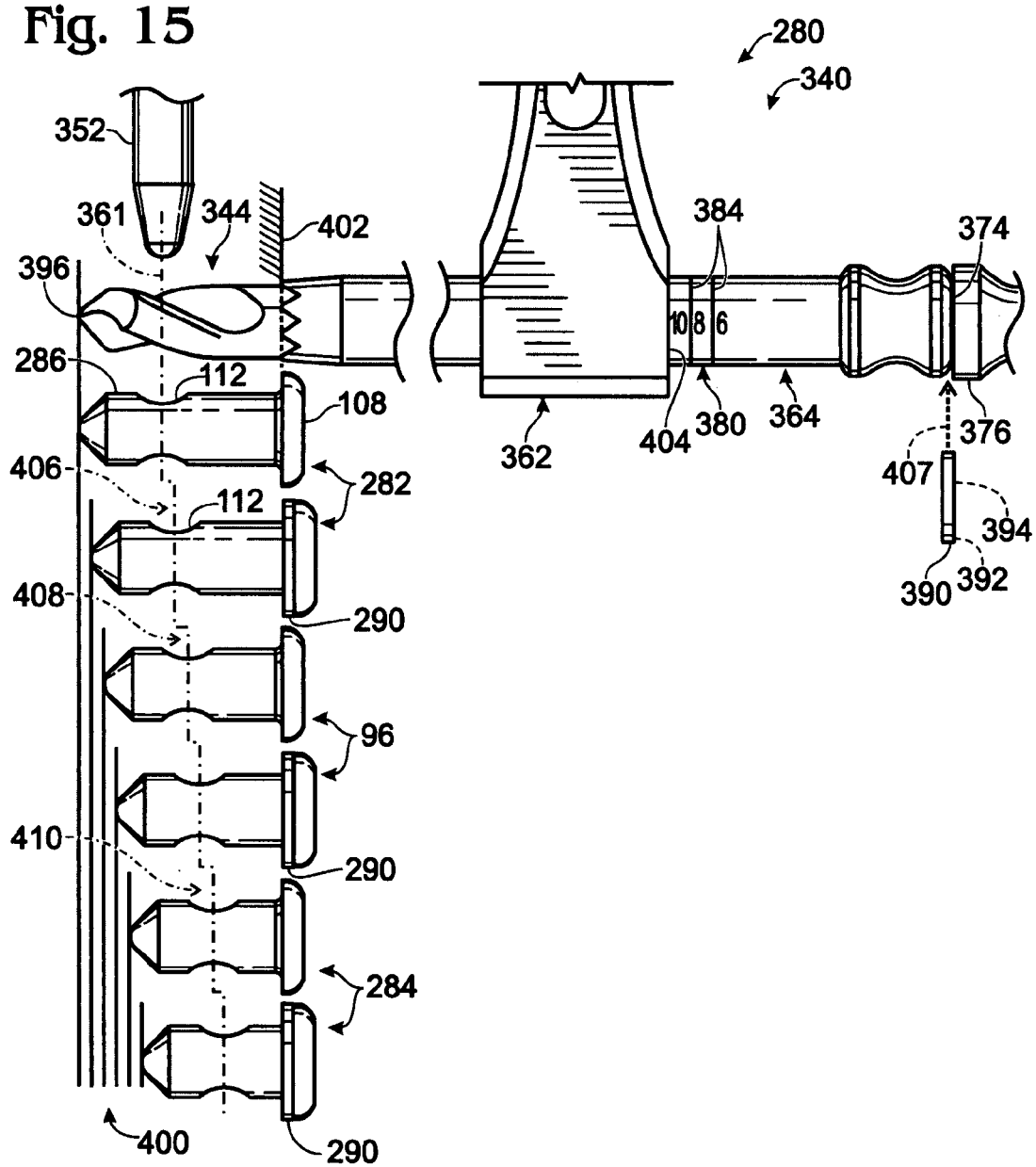
FIG. 15 is a fragmentary view of a guide assembly from the system of FIG. 14 aligned with transverse fasteners of different length from the system of FIG. 14 to illustrate how the guide assembly may be used (a) to measure a radial dimension of a bone, (b) to adjust the depth of drilling into bone, and/or (c) to indicate an appropriate fastener size for installation, in accordance with aspects of the present disclosure.

FIG. 15 shows guide assembly 340 of system 280 arranged adjacent a paired series of transverse fasteners 282, 96, 284. Each fastener pair has a member assembled with spacer element 290 and a member lacking the spacer element, to provide a fastener series with effective aperture 112 positions that differ incrementally, such as by increments, indicated at 400, of one millimeter, among others. The fasteners are shown aligned with respect to a bone surface 402, that is, with the undersides of the fastener heads aligned. (The heads may be unitary (e.g., without spacer element 290) or formed by two or more pieces (e.g., integral head 108 plus spacer element 290).

The guide assembly is shown with stem 352 defining a central long axis 361 relative to bone surface 402. In addition, in this view drill 344 is fully advanced in guide element 364, such that flange 376 is abutted against trailing end 374 of the guide element (i.e., without any spacers 390, 392 or 394 disposed between flange 376 and trailing end 374). Accordingly, tip 396 of the drill is advanced fully beyond the bone surface to drill the deepest hole permitted by this assembly. Transverse fastener 282 (without spacer element 290) may have a shaft 286 with a length that corresponds to the depth of the hole, with transverse aperture 112 positioned, in this example, ten millimeters from the fastener head. Indicia 380 on guide element 364 may indicate, by the number "10" juxtaposed to reference structure 404 of frame 362, that the measured radial dimension of the bone is ten millimeters, that fastener 282 is suitable for placement into the drilled hole, and that drilling should be performed without the use of any spacers 390-394. Selection of fastener 282 may be facilitated by indicia on the fastener, such as the number "10" or corresponding identifying information. The specific fastener sizes and size-descriptive indicia presented here and elsewhere in the present disclosure are intended to be illustrative only and are not intended to limit the scope of the present disclosure.

The lower portion of FIG. 15 shows how central long axis 361 of stem 352 would be shifted closer to bone surface 402 for distinct bones having incrementally smaller local radial dimensions, with axis 361 extending through transverse apertures 112 of the remaining transverse fasteners. Each incremental shift in the spacing between axis 361 and bone surface 402 may result in a corresponding change in the relative positions of guide element 364 and frame 362, with the guide element engaged with the bone surface.

A one millimeter shift, shown at 406, may result in reference structure 404 shifting to a position halfway between graduations (reference marks) 384 for "10" and "8." Accordingly, a practitioner (a user) may, by interpolation, read this shift from indicia 380 as "9" and may place a one-millimeter spacer 390 onto leading section 372 of drill 344, indicated schematically at 407, to decrease the depth of drilling by one millimeter. In addition, the practitioner may place transverse fastener 282 assembled with spacer element 290 into the corresponding transverse hole formed in bone (decreased in depth by spacer 390).

An additional one millimeter shift in the radial dimension of the bone, shown at 408, may result in reference structure 404 shifting to the reference mark for "8." Accordingly, a practitioner may read "8" from indicia 380 and place two-millimeter spacer 392 (without spacer 390) onto leading section 372 of drill 344, to decrease the depth of drilling by two millimeters (based on a measured eight millimeter radial dimension in the present illustration). In addition, after drilling, the practitioner may place transverse fastener 96 (without spacer element 290) into the transverse hole formed by drill 344 in the presence of spacer 392.

An additional two millimeter shift in the radial dimension, shown at 410, may result in reference structure 404 shifting to the reference mark for "6." Accordingly, a practitioner may read "6" from indicia 380 and place four-millimeter spacer 394 onto leading section 372 of drill 344 (without any other spacers), to decrease the depth of drilling by four millimeters (based on a measured radial dimension of six millimeters in the present illustration). In addition, the practitioner may place transverse fastener 284 (without spacer element 290) into the transverse hole formed by drill 344 while decreased in depth by spacer 394.

VII. METHODS OF FIXING AND/OR COMPRESSING BONES

The present disclosure provides methods of fixing bones and/or compressing bones longitudinally. The methods may include any of the steps presented below or elsewhere in the present disclosure. The steps may be performed in any suitable order, in any suitable combination, and each step may be performed any suitable number of times. FIGS. 16-23 show illustrative configurations produced during performance of an illustrative method of fixing and/or compressing bones according to aspects of the present disclosure. These figures will be referred to in the following discussion of illustrative methods.

A bone may be selected for fixation. Any suitable bone (or bones for a fusion procedure) may be selected. Accordingly, the bone may be a long bone or another bone of the skeleton. The bone selected may be a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, and/or the like. The bone may have a discontinuity. The discontinuity may be a pre-existing discontinuity present before surgery and/or a discontinuity introduced during performance of a method of bone fixation and/or compression. Accordingly, the methods may include a step of introducing a discontinuity into the selected bone, such as by cutting or breaking the bone. The bone may have any suitable condition to be treated, including a fracture, a cut, a malunion, a nonunion, a structural weakness, an undesirable length and/or angulation, and/or the like. The condition may affect any suitable portion of the bone, such as a diaphyseal (shaft or central) and/or a metaphyseal (end) region of the bone. In some embodiments, the bone may have a discontinuity introduced during surgery to access an adjacent injured bone. For example, a subject may have an injured distal humerus, which may be accessed for repair by introducing a discontinuity into an olecranon region of the adjacent ulna (e.g., by performing an osteotomy). The discontinuity may provide access to underlying bone by allowing movement of soft tissue, such as the triceps muscle/tendon, away from bone.

In some embodiments, the methods may include creating an incision through soft tissue to access the bone. The step of creating an incision may create one or more incisions at any suitable position(s) relative to the selected bone. For example, an incision may be created near an end of a bone (e.g., the proximal end or the distal end of the bone), particularly near a central long axis defined by the bone and/or the medullary canal of the bone (e.g., to allow formation of a longitudinal hole and/or installation of a collar and/or rod). The incision may allow a practitioner to access an end surface region of the bone that overlaps the central long axis. Optionally, at least a second incision may be created to access a side of the bone (e.g., to allow formation of a transverse hole and/or installation of a transverse fastener). The second incision may be created before or after an incision is created near the end of the bone, or the same incision may be used to access the end and the side of the bone, such that only one incision is created for installation. The second incision (or the single incision) may be created to access any suitable side of the selected bone, such as the anterior, posterior, medial, and/or lateral side of the bone. In some embodiments, the second incision may be created to access the ulna posteriorly and/or in a direction generally from the midline of the body (i.e., to access the ulnar or inner surface region of the ulna generally closest to the midline of the body), among others. These and other suitable steps of the methods may be performed under sterile conditions and/or in a sterile field, for example, during surgery in an operating room.

The methods may include a step of forming a hole in an end region of the selected bone. The step of forming a hole may include a step of penetrating the bone to access the medullary canal. The step of forming a hole also may include a step of forming a hole longitudinally in the bone, particularly the medullary canal thereof. The hole may be of generally uniform diameter along most or all of its length, and/or may taper toward the leading end of the hole, among others. In some embodiments, the step of forming a hole may include a step of forming a hole that is wider toward the end of the bone and/or a step of widening a hole near the end of the bone. The step of widening the hole near the end of the bone may form a widened region of substantially uniform diameter or may form a widened region that tapers toward the leading end of the hole. The hole may extend any suitable distance into bone. For example, the hole may extend a distance that is less than, about the same as, or greater than the length of the rod (e.g., rod 92) of the fixation device. In some embodiments, the hole may extend a distance that is about one-half the length of the rod or about the length of the rod from its head to its threaded region.

Figure 16:
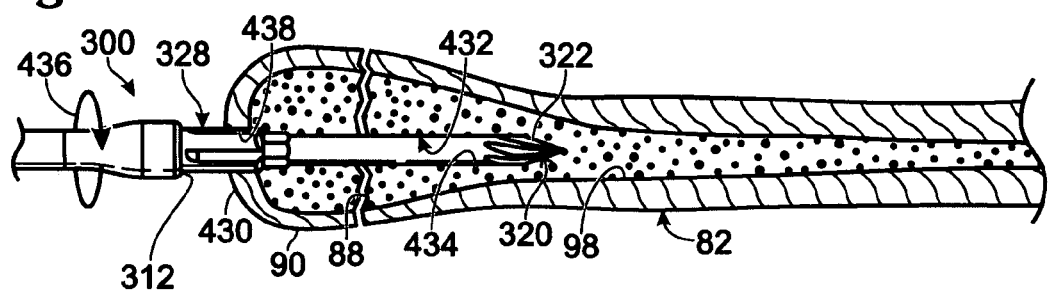
FIG. 16 is a fragmentary view of a left ulna sectioned coronally and fractured in an olecranon region of the ulna, with a drill being used to form a hole in the ulna during performance of an illustrative method of fixing bone using the system of FIG. 14, in accordance with aspects of present disclosure.

FIG. 16 shows an illustrative hole being formed in a selected bone. Here, the selected bone is left ulna 82 with fracture 88 in olecranon region 90 of the ulna. A proximal portion of ulna 82 is shown, sectioned coronally. Tool 300 may be advanced longitudinally into medullary canal 98 of ulna 82 from end region 430 to form a longitudinal hole 432. In particular, awl structure 328, including pointed tip 322 and its cutting edges, may be used to penetrate the end of the bone and then to form a cylindrical portion 434 of longitudinal hole 432, such as by turning tool 300, as indicated at 436, and urging the tool into the bone. Optionally, reamer structure 328 may be used to widen the longitudinal hole to form a widened portion 438 near a trailing end of the longitudinal hole. In some embodiments, advancement of tool 300 may be stopped when stop structure 312 abuts end region 430 of the bone. Distinct regions of hole 432 may be formed using the same tool, as shown here, or may be formed by at least two distinct tools, such as a first tool to form cylindrical portion 434 and a second tool to form widened portion 438.

A collar may be installed longitudinally in the bone. Installation may include driving the collar translationally and/or rotationally to introduce at least a portion, most, or all of the collar into the bone. Accordingly, installation of the collar may include pushing or hammering the collar into bone and/or turning the collar into threaded engagement with the bone. The collar may be installed such that a central long axis of the hole formed in bone extends through an opening of the collar and/or is collinear with the central axis of the opening (such that the hole and the collar are concentric). In alternative embodiments, the collar may be disposed partially, at least mostly, or substantially exclusively on bone rather than being installed only in the bone. In some embodiments, the collar may be installed using a driver that extends forward of the collar, longitudinally in bone. For example, the driver may extend along a longitudinal hole formed in bone, such as to ensure that the collar is installed in alignment with the longitudinal hole.

Figure 17:
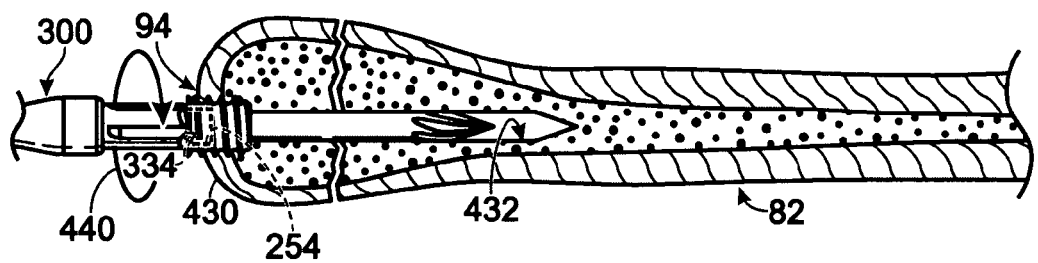
FIG. 17 is a fragmentary view of the left ulna of FIG. 16, with a collar of the fixation device being driven into the proximal end of the ulna during performance of an illustrative method of fixing bone using the system of FIG. 14, in accordance with aspects of the present disclosure.

FIG. 17 shows a configuration produced during an illustrative installation of a collar in bone. Here, collar 94 is being driven into threaded engagement with end region 430 of ulna 82 using tool 300. In particular, after formation of longitudinal hole 432, tool 300 may be removed from bone and collar 94 placed on the tool such that driver portion 334 of the tool is received by driver-engagement structure 254 of the collar (also see FIGS. 12-14). Tool 300 may be rotated, indicated at 440, to advance collar 94 into the widened region of hole 432.

A radial dimension of the selected bone may be measured. The radial dimension may be measured by a guide device or by a distinct measuring device that is distinct from the guide device. The radial dimension may be measured near a position at which a transverse hole is to be formed in bone.

Figure 18:
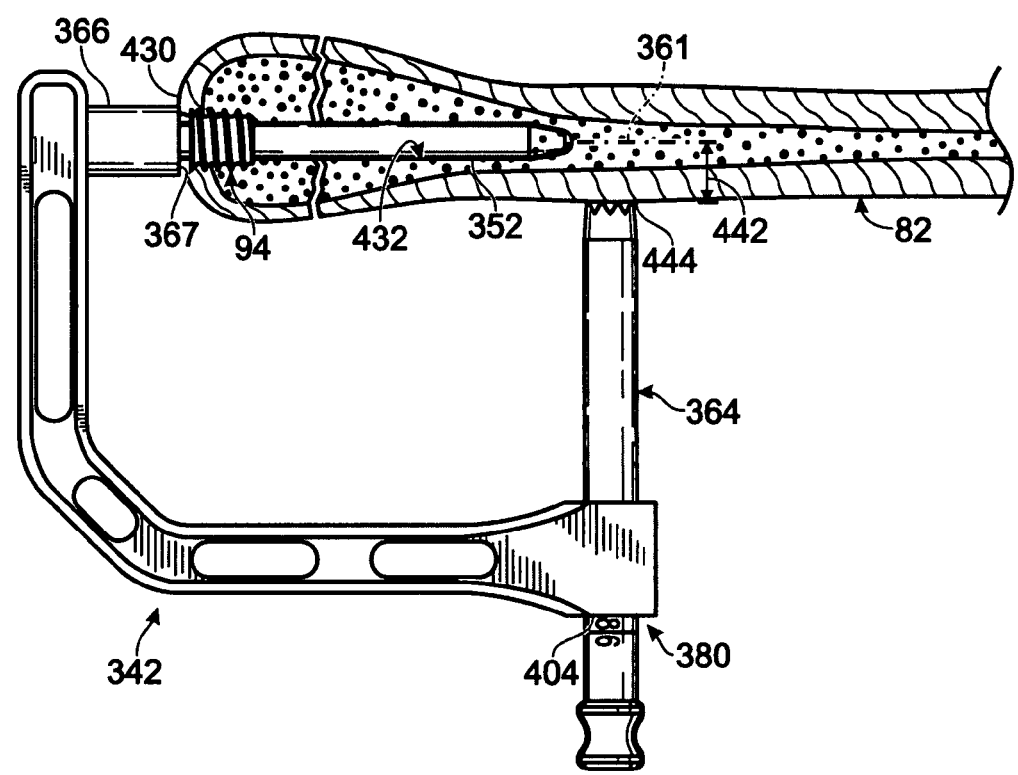
FIG. 18 is a fragmentary view of the left ulna of FIG. 16, with a guide device coupled to the ulna to guide formation of a transverse hole and also to guide selection of a fastener for the transverse hole during performance of an illustrative method of fixing bone using the system of FIG. 14, in accordance with aspects of the present disclosure.

FIG. 18 shows a configuration produced during an illustrative measurement of a radial dimension 442 of ulna 82. However, the illustrative measurement may be performed on any other suitable bone. Guide device 342 may be coupled to the ulna using longitudinal hole 432. For example, stem 352 of the guide device may be inserted into longitudinal hole 432, such that the stem is aligned with the central long axis of hole 432. The longitudinal position of stem 352 may be determined by stop structure 366 of the guide device. In particular, stem 352 may be advanced until shoulder 367 of stop structure 366 engages end region 430 of ulna 82 (and/or the end of collar 94). In some embodiments, stem 352 may include a reference mark to indicate where longitudinal advancement of the stem should be stopped (and/or a plurality of reference marks to permit selection of a suitable degree of longitudinal advancement), and/or the longitudinal position of the stem may be selected with stop structure 366 spaced from bone, to adjust the longitudinal position along bone for transverse drilling and fastener placement. An angular disposition of the guide device may be selected by pivoting the guide device about central long axis 361 defined by stem 352. The angular disposition may be selected before and/or after the stem has been inserted into bone or the angular disposition may be predetermined by a structure of the collar. Selection of the angular disposition may select a side and/or surface position 444 of the bone at which the radial dimension is to be measured (and/or a transverse hole is to be formed). Guide element 364 also may be advanced into engagement with ulna 82. In other embodiments, the guide device may be coupled to bone via the rod (e.g., rod 92).

Radial dimension 442, corresponding to the distance from stem axis 361 (and/or the central long axis of longitudinal hole 432) to surface position 444, then may be read from indicia 380 of guide element 364. For example, here, the number "8" may be read from indicia 380 based on the position of the "8" relative to reference structure 404. The measurement read from indicia 380 may correspond to radial dimension 442, such as describing the radial dimension numerically (e.g., "8" for eight millimeters) or in any other suitable form (e.g., in correspondence with indicia on a set of fasteners of different length and/or with different transverse aperture positions).

A transverse hole may be formed in bone. The transverse hole may be formed at any suitable time, such as before or after formation of a longitudinal hole in bone and/or before or after installation of an optional collar of the fixation device. The transverse hole may be orthogonal or oblique to a longitudinal hole formed in bone. In addition, the transverse hole may intersect the longitudinal hole or may be spaced from the longitudinal hole. The transverse hole may have any suitable length (depth). For example, the transverse hole may extend only partially across the bone or may extend completely through the bone crosswise. The transverse hole may intersect the medullary canal of the bone and may extend only unicortically into bone or may be extend bicortically such that transverse hole spans the medullary canal crosswise. The transverse hole may have any suitable diameter, generally a diameter that corresponds to the diameter of the shaft of a fastener to be placed into a transverse hole and that is larger than the diameter of the longitudinal hole formed in bone and/or larger than the diameter of the threaded region of the rod (e.g., rod 92). The transverse hole may be formed with a hole-forming tool that is driven manually or power-driven. Furthermore, formation of the transverse hole may be guided by a guide device disposed at least partially in bone. In particular, formation of the transverse hole may be guided by a guide device partially received in the medullary canal of the bone, such as partially received in a longitudinal hole formed in bone. Accordingly, a guide path may be defined and a transverse hole formed in bone and along the guide path without the fixation rod (e.g., rod 92) disposed in bone.

Figure 19:
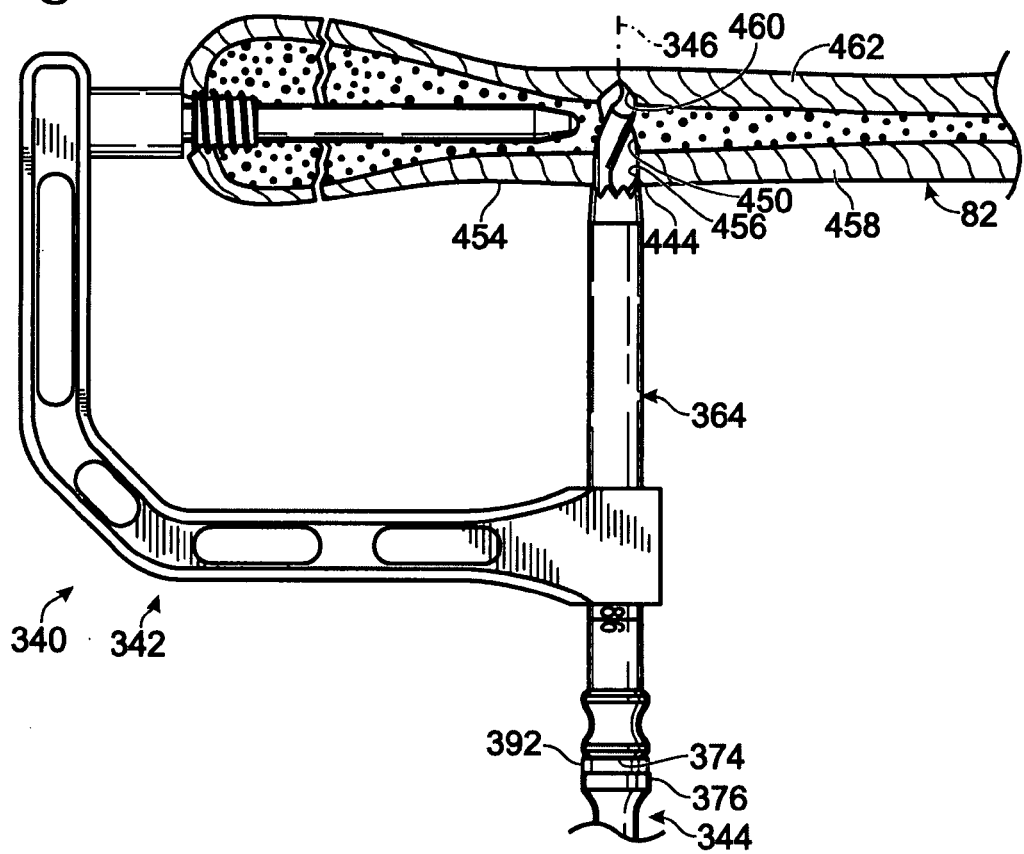
FIG. 19 is a fragmentary view of the left ulna of FIG. 16, with the guide device of FIG. 18 guiding formation of the transverse hole during performance of an illustrative method of fixing bone using the system of FIG. 14, in accordance with aspects of the present disclosure.

FIG. 19 shows a configuration produced during illustrative formation of a transverse hole 450 in ulna 82 using guide assembly 340. Guide device 342 of the assembly may define a guide path or guide axis 346 for forming transverse hole 450. Guide axis 346 may be defined near the site at which a radial dimension of the bone was measured (i.e., at surface position 444). Drill 344 may be received in guide element 364 and advanced along guide axis 346 into ulna 82. Advancement of the drill may be restricted mechanically and/or based on observation of one or more visible marks by a practitioner. Here, advancement of the drill is restricted mechanically by engagement of components of guide assembly 340. In particular, drill 344 may contact guide element 364 directly, such as via trailing end 374, to stop advancement, or advancement of drill 344 may be stopped by engagement of a spacer(s), such as spacer 392, with flange 376 and trailing end 374 of the guide element. In some embodiments, a suitable spacer (or lack of spacer) may be selected based on a measured radial dimension of the bone. For example, here, spacer 392 is being used to reduce the depth of drilling by two millimeters based on an intermediate radial dimension ("8") indicated by the guide device. Drilling may be performed by rotating drill 344.

Transverse hole 450 may extend into ulna 82 from an ulnar side 454 and/or a posterior side (among others) of the ulna. Transverse hole 450 may include a through-hole portion 456 through a near cortex region 458 of the ulna and a blind-hole portion (or a through-hole portion) 460 into (and/or through) a far cortex region 462 of the ulna.

A fastener may be placed crosswise into bone. The fastener may be placed into a preformed hole in bone or may be self-drilling such that the fastener forms a hole for itself as it is advanced into bone. The fastener may be placed in a transverse hole that is about the same depth as the length of the shaft of the fastener. Alternatively, the fastener may be placed into a transverse hole that is shallower or deeper than the length of the shaft. Placement of the fastener may be performed by manual engagement of the fastener or using a tool or holder that engages the fastener. Placement of the fastener may include orienting the fastener via the holder. In particular, the fastener may be oriented by aligning an indicator structure, such as an indicator arm, with the long axis of the bone. In some embodiments, the fastener may include an external thread and may be driven into bone by turning the fastener.

Figure 20:
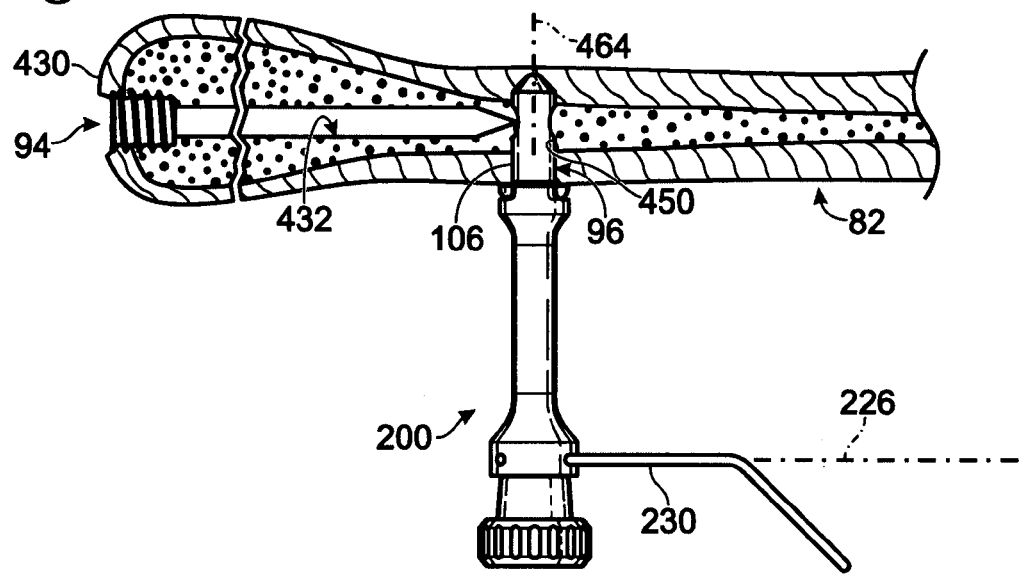
FIG. 20 is a fragmentary view of the left ulna of FIG. 16, with a fastener disposed in the transverse hole in the ulna and mounted on the holder of FIG. 9 during performance of an illustrative method of fixing bone using the system of FIG. 14, in accordance with aspects of the present disclosure.

FIG. 20 shows a configuration produced during illustrative placement of transverse fastener 96 into transverse hole 450 of ulna 82. Fastener 96 may be mounted on holder 200, before or after placement of the fastener into the transverse hole, such that motion of the fastener and holder are coupled. Accordingly, fastener 96 may be pushed into hole 450 via force exerted on holder 200, after uncoupling the guide device from bone (e.g., by removing the internal portion of the guide device from the ulna). In addition, the pivotal orientation of fastener 96 about a central axis 464 defined by shaft 106 may be determined and/or adjusted based on holder arm 230. In particular, axis 226 of arm 230 may be aligned with the long axis of ulna 82 and/or with hole 432 by pointing arm 230 generally toward either opposing end of ulna 82 and/or generally parallel to the long axis of the bone. For example, here, arm 230 is pointed toward the distal end of the ulna (i.e., toward the hand), and away from proximal end region 430 and collar 94. The orientation indicator of the holder may be engaged and/or grasped by hand to orient the holder and fastener.

A rod of the fixation device may be installed in the bone such that the rod is locked to the fastener, for example, by threaded engagement with the fastener. Installation may include placement of a body of the rod through the collar and engagement of the collar with a head of the rod. If a guide device is used to form a transverse hole, the rod may be placed after uncoupling the guide device from bone and/or removing an internal portion of the guide device from the medullary canal. Installation also may include placement of the rod longitudinally into bone such that a leading section of the rod travels through a transverse aperture of the fastener until a threaded region of the rod abuts the fastener. The leading section of the rod may be structured to include one or more flared regions such that the rod fits more tightly in the transverse aperture as the leading section is advanced into abutment with the threaded region. Furthermore, the leading section may be structured to provide confirmation that the rod has been received by the fastener. In particular, the leading section may be structured such that the rod can be advanced translationally by an additional confirmation distance into bone (and past the fastener), but only if a tip portion of the leading section has been received successfully in the aperture. The confirmation distance may be at least about as great as the diameter of the shaft of the fastener. The rod then may be advanced farther by rotating the rod into threaded engagement with the fastener, such that the head of the rod abuts the collar (and/or an end region of bone) and the bone is compressed longitudinally.

Figure 21:
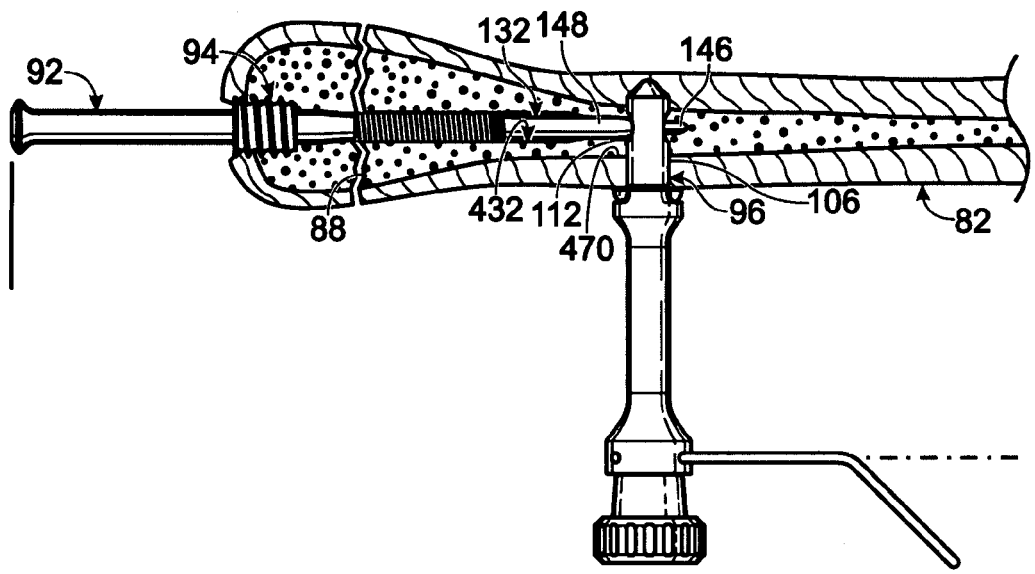
FIG. 21 is a fragmentary view of the left ulna of FIG. 16, with a leading section of the rod being advanced through an aperture of the fastener during performance of an illustrative method of fixing bone using the system of FIG. 14, in accordance with aspects of the present disclosure.
Figure 22:
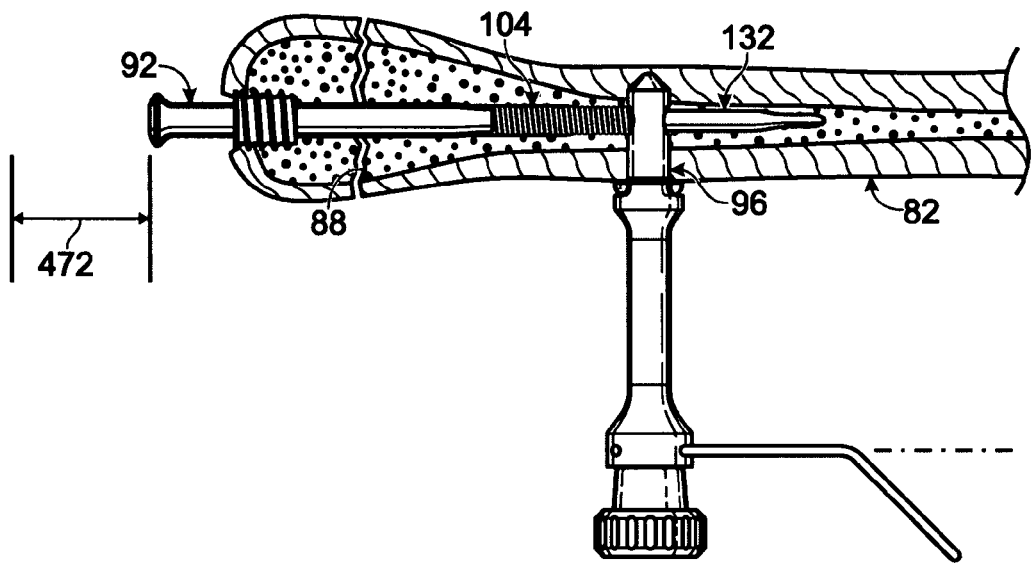
FIG. 22 is a fragmentary view of the left ulna of FIG. 16, with the leading section of the rod fully advanced to indicate proper alignment of the rod and fastener prior to threaded engagement during performance of an illustrative method of fixing bone using the system of FIG. 14, in accordance with aspects of the present disclosure.
Figure 23:
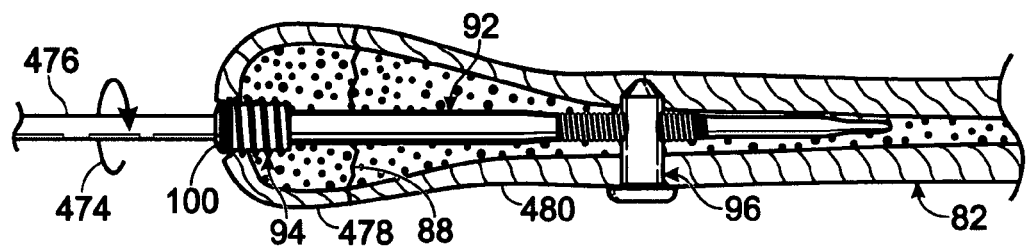
FIG. 23 is a fragmentary view of the left ulna of FIG. 16, with the rod in threaded engagement with the fastener and with the ulna compressed longitudinally during performance of an illustrative method of fixing bone using the system of FIG. 14, in accordance with aspects of the present disclosure.

FIGS. 21-23 show configurations produced during illustrative placement of rod 92 longitudinally into ulna 82, along longitudinal hole 432 and into threaded engagement with transverse fastener 96.

FIG. 21 shows rod 92 extending through collar 94 with tip portion 146 of leading section 132 received in and extending past aperture 112 of the transverse fastener. At this point of rod placement, a practitioner may not be certain where tip portion 146 is disposed relative to aperture 112. For example, tip portion 146 may have missed the aperture, with a disposition lateral to the transverse fastener, between shaft 106 and cortical wall 470. However, leading section 132 may be structured to distinguish between placement of the rod on-target and off-target. In particular, leading section 132 may flare one or more times rearward of the tip portion to form an intermediate portion 148 of greater diameter than the tip portion that provides a confirmation distance of advancement of the rod. Accordingly, if the rod has been placed off target and has missed the transverse aperture, the diameter of intermediate portion 148 may be large enough to restrict advancement of the intermediate portion past the transverse fastener.

FIG. 22 shows rod 92 with leading section 132 fully advanced to indicate proper alignment of the rod and fastener 96 prior to threaded engagement. In this configuration, threaded region 104 may be abutted with fastener 96 (but not in threaded engagement with the fastener) and the rod may be substantially more constrained laterally than the configuration shown in FIG. 21, due to the increased diameter of the rod adjacent the threaded section relative to the tip portion of the rod. Furthermore, the rod may have advanced a confirmation distance 472 into bone, such that the length of rod disposed outside of bone is reduced by the confirmation distance relative to only the tip portion being received in aperture 112 of the transverse fastener (see FIG. 21). Proper alignment of the rod and fastener may be confirmed by an imaging technique, generally with X-rays, such as via a fluoroscope or the like. Confirmation distance 472 may be selected to be noticeable to the practitioner, such as at least about one-half or one centimeter, among others. Alternatively, or in addition, the practitioner may determine that the rod is seated properly for threaded engagement by its restricted freedom of lateral movement.

FIG. 23 shows rod 92 in threaded engagement with fastener 96 and with ulna 82 compressed longitudinally. Rod 92 may be turned, indicated at 474, by a driver 476 engaged with head 100 of the rod. As the rod is advanced after initial engagement of head 100 with collar 96 (and/or bone), a proximal portion of ulna 82 may be compressed longitudinally, to, for example, urge an end fragment 478 of ulna 82 toward a main fragment 480 of the ulna, thereby reducing a gap, if any, between the fragments (e.g., compare fracture 88 in FIGS. 22 and 23).

Fixation and/or longitudinal compression may be adjusted by turning the rod such that the head of the rod moves toward or away from transverse fastener 96.

VIII. COMPOSITION OF SYSTEM COMPONENTS

The orthopedic fixation devices (i.e., the rods, transverse fasteners, and collars) and/or any other system components disclosed herein may be formed of any suitable biocompatible material(s) and/or bioresorbable (bioabsorbable) material(s). Illustrative biocompatible materials that may be suitable for the rod, transverse fastener, collar, and/or other system components include (1) metal (for example, titanium or titanium alloys, cobalt-chrome alloys, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramic (for example, alumina, beryllia, calcium phosphate, and/or zirconia, among others); (4) composite (for example, carbon-fiber composites); (5) bioresorbable material or polymer (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone material or bone-like material (e.g., bone chips, calcium phosphate crystals (e.g., hydroxyapatite, carbonated apatite, etc.); and/or the like. In some examples, one or more of these materials may form the body or core of a component and/or a coating thereon.

The components of a fixation device may be formed of the same or different materials. For example, the components each may be formed of metal, of the same or different composition, or one or more (or all) of the components may be formed of a non-metal material, such as a plastic, ceramic, and/or bioresorbable material.

IX. EXAMPLES

The following examples describe selected aspects and embodiments of the present disclosure, particularly fixation devices with illustrative structure. These examples and the various features and aspects thereof are included for illustration and are not intended to define or limit the entire scope of the present disclosure.

Example 1

Illustrative Rod and Collar

This example describes an illustrative rod 500 and collar 502 that may be used in the fixation systems of the present disclosure; see FIGS. 24-26.

Rod 500 may include a head 504 connected to a body 506 by a neck 508. Body 506 may extend generally from neck 508 to leading end 510. The body may include a trailing section 512 with a threaded region 514 and a leading section 516 extending from a forward boundary 518 of the trailing section to leading end 510.

Trailing section 512 may include a tail or butt region 520 that extends from a trailing boundary 522 of threaded region 514 to neck 508 (or to head 504 if the neck is not present). Tail region 520 may have about the same diameter as the major diameter of threaded region 514 or may be wider than the threaded region, such as at least about one and one-half or at least about twice as wide as the threaded region. The tail region may be shorter than, about the same length as, or longer than the threaded region. For example, here, the tail region is substantially longer than the threaded region, namely, at least about twice as long as a threaded region. Tail region 520 may have no surface relief structure, as shown here, or may include projections or depressions, such as ridges, grooves, dimples, and/or bumps, among others. In some embodiments, tail region 520 may include a thread that is distinct from the external thread of threaded region 514.

Leading section 516 may include an extended tip portion 523 and a flared region 524 that provides a transition from the tip portion to threaded region 514. Tip portion 523 (and/or the leading section) may be substantially longer than the major diameter of threaded region 514, such as at least about 2, 3, or 5 times longer than the major diameter, among others. Tip portion 523 (and/or the leading section) also or alternatively may have a length that is at least a substantial portion of the length of the threaded region, such as at least about one-fourth or at least about one-half the length of the threaded region, or at least about the same length as the threaded region. Tip portion 523 may have a substantially uniform diameter to, for example, provide a cylindrical tip portion, or the tip portion may vary in diameter along its length.

Neck 508 may have any suitable structure. For example, the neck may have about the same length as the axial length of the head, measured parallel to the long axis of the rod. Alternatively, the length of the neck may be less than or greater than the axial length of the head. The diameter of the neck may be substantially narrower than tail region 520, such as less than about one-half the diameter of tail region 520. Neck 508 may have an angular and/or curved profile.

FIGS. 25 and 26 show collar 502 in respective plan and sectional views. Collar 502 may have a generally planar structure (e.g., shaped as a washer) with a body 526 defining a central opening 528. The central opening may be sized to be received on rod 500 from leading end 510 and restricted from advancing past head 504 of the rod. Opening 528 have any suitable shape. For example, the opening may be at least partially cylindrical, indicated at 530, or may flare toward an outer face of 532 (as shown here) and/or toward an inner face 534 of the collar.

Collar 502 also may include one or more projections 536, such as cleats 538, extending from inner face 534 of the collar. Projections 536 may be structured to engage and/or penetrate bone and thus may be pointed, as shown here. The projections may be arranged around the collar, such as adjacent a perimeter of the collar, at any suitable number of positions, such as at least one, two, three, four, or more positions. The projections may extend away from inner face 534, such as generally orthogonally or obliquely to the inner face.

Example 2

Illustrative Beveled Collar

This example describes an illustrative beveled collar 540 that may be included in the fixation systems of the present disclosure; see FIG. 27.

Collar 540 may include a root portion 542 defining a central passage 544 and also may include an external thread 546 formed on the root portion. External thread 546 (and/or root portion 542) may taper toward a leading end 548 of the collar or may have a substantially uniform major diameter along the collar. Furthermore, the collar may have a beveled trailing end 550 disposed obliquely to a central axis 552 of the collar. The trailing end thus may define a plane that extends at any suitable angle from orthogonal to central axis 552, such as a least about 5, 10, or 20 degrees, among others, from orthogonal. A trailing end that is not square to central axis 552 may provide a better match of the trailing end to an angled end of a bone, such as a proximal end of the ulna, which may be disposed obliquely relative to the long axis of the bone. Accordingly, when collar 540 is installed, the collar may be driven into bone and then adjusted by turning the collar less than about one full turn, until trailing end 550 has an angular disposition that most closely matches the angular disposition of the surrounding bone surface.

Example 3

Illustrative Transverse Fastener and Holder

This example describes another illustrative fastener 560 and holder tool 562 that may be included in a system for bone fixation; see FIG. 28.

Fastener 560 may be structured generally as described above for fastener 96 except that fastener 560 may include a different head 564. The head may define one or more recesses 566 for receiving a portion of holder tool 562. In particular, holder tool 562 may be structured generally as described above for holder 200 (see FIGS. 9 and 10) except that holder tool 562 may include a body portion 568 with mating structure 570, such as one or more pins 572 or other projections that are structured and arranged to be received in recesses 566 of the fastener. Fastener 560 may be fixed in position after pins 572 are received in recesses 566 using securing portion 204, generally as described above in relation to FIGS. 9 and 10. Head 564 of the fastener may have two-fold rotational symmetry, as shown here, may have higher order rotational symmetry, for mating with holder tool 562 in three or more permitted angular dispositions, or may have no rotational symmetry, such that fastener 560 only can be mated with holder tool 562 in one angular disposition. Head 564 may have a circular or noncircular shape, as appropriate or desired.

Example 4

Illustrative Collar with Flared Root Portion

This example describes still yet another illustrative collar 580 that may be used in the fixation devices of the present disclosure; see FIGS. 29-31.

Collar 580 may include a root portion 582 with an external thread 584 formed on the root portion. Root portion 582 may provide a nonuniform minor diameter to the collar. In particular, root portion 582 may flare, indicated by dashed lines at 586, toward a trailing end 588 of the collar. The root portion may change in diameter over any suitable portion of the collar, such as becoming wider over the entire length of the collar or becoming wider selectively near trailing end 588. Accordingly, helical groove 590 may become shallower toward the trailing end of the collar, which may be occur over any suitable number of turns of the helical groove, such as becoming shallower over at least about two turns, less than about two turns, or less than about one turn, among others. A shallower helical groove may function to restrict advancement of collar 580 into bone, by increasing the resistance to turning the collar. As a result, the flared root portion may restrict over-advancement of the collar into bone.

Root portion 582 may define a central passage 592 that extends through the collar. Central passage 592 may have any of the features described above in relation to FIGS. 11-13.

Example 5

Selected Embodiments I—Guide Device

This example describes selected embodiments of the present disclosure, presented as a series of indexed paragraphs. In particular, this example describes bone fixation apparatus and methods that include and/or use a guide device.

1. A system for bone fixation, comprising: (A) a fixation device including (i) a rod for placement longitudinally into a medullary canal of a bone, (ii) a fastener for placement into a transverse hole in the bone that intersects the medullary canal, the fastener defining an aperture that receives a portion of the rod such that the rod engages the fastener to lock the rod to the fastener; and (B) a guide device that couples to the bone to guide formation of the transverse hole in the bone.

2. The system of paragraph 1, wherein the rod includes an external thread and locks to the fastener by threaded engagement of the external thread with the fastener.

3. The system of paragraph 1, wherein the guide device has an internal portion for placement longitudinally into the medullary canal and an external portion that defines a transverse path for formation of the transverse hole in the bone, and wherein the internal portion defines a long axis that intersects the transverse path.

4. The system of paragraph 3, wherein the internal portion of the guide device is configured to be removed from the medullary canal before the rod is placed longitudinally into the medullary canal.

5. The system of paragraph 3, wherein the guide device is configured to define a transverse path for hole formation that does not intersect the internal portion of the guide device.

6. The system of paragraph 1, wherein the guide device is configured to measure a radial dimension of the bone.

7. The system of paragraph 1, wherein the guide device includes a frame and at least one guide element defining a passage for receiving a hole-forming tool that forms the transverse hole in the bone.

8. The system of paragraph 7, wherein the at least one guide element is slidable in relation to the frame and includes indicia that correspond to different radial dimensions of a bone.

9. The system of paragraph 1, wherein the rod is substantially inflexible.

10. A system for bone fixation, comprising: (A) a fixation device including (i) a rod for placement longitudinally into a medullary canal of a bone, the rod including a head and a body, the body including an external thread, (ii) a fastener for placement into a transverse hole in the bone that intersects the medullary canal, the fastener defining an aperture with an internal thread for threaded engagement with the external thread of the rod; and (B) a guide device including an internal portion for placement longitudinally into the medullary canal along a placement axis such that an external portion of the guide device defines a guide axis intersecting the placement axis for guiding a tool that forms the transverse hole in the bone.

11. The system of paragraph 10, wherein the rod and the internal portion of the guide device are configured to occupy overlapping regions of the medullary canal in a mutually exclusive fashion.

12. A method of bone fixation, comprising: (A) coupling a guide device to a bone to define a transverse path across the bone and intersecting the medullary canal of the bone; (B) forming a transverse hole in the bone along the transverse path; (C) disposing a fastener with an aperture in the transverse hole; and (D) placing a rod longitudinally in the medullary canal such that a portion of the rod enters the aperture and engages the fastener to lock the rod to the fastener.

13. The method of paragraph 12, wherein the step of coupling a guide device is performed before the step of placing a rod.

14. The method of paragraph 12, wherein the step of coupling a guide device includes a step of disposing a portion of the guide device in the medullary canal of the bone.

15. The method of paragraph 14, wherein the step of disposing a portion of the guide device includes a step of placing an internal portion of the guide device longitudinally into the medullary canal along a placement axis such that an external portion of the guide device defines the transverse path to intersect the placement axis.

16. The method of paragraph 14, further comprising a step of removing the portion of the guide device from the medullary canal of the bone before the step of placing a rod.

17. The method of paragraph 14, wherein the step of disposing a portion of the guide device includes a step of advancing a portion of the guide device into the medullary canal until a stop structure of the guide device restricts further advancement of the portion.

18. The method of paragraph 14, wherein the step of disposing a portion of the guide device defines a transverse path that does not extend through the portion of the guide device.

19. The method of paragraph 14, further comprising a step of forming a longitudinal hole in the medullary canal for receiving the portion of the guide device, wherein the step of disposing a portion of the guide device includes a step of placing the portion of the guide device into the longitudinal hole.

20. The method of paragraph 12, wherein the step of placing a rod includes a step of locking the rod to the fastener, further comprising a step of uncoupling the guide device from the bone before locking the rod to the fastener.

21. The method of paragraph 12, wherein the step of placing a rod includes a step of disposing the rod in threaded engagement with the fastener.

22. The method of paragraph 12, further comprising a step of measuring a radial dimension of the bone using, at least in part, the guide device.

23. The method of paragraph 22, further comprising a step of selecting a fastener from a set of fasteners of different size based on the step of measuring a radial dimension of the bone, wherein the fastener selected is used in the step of disposing a fastener.

24. The method of paragraph 12, further comprising a step of installing a collar for the rod in and/or on the bone, wherein a portion of the rod is advanced through the collar during the step of placing a rod, and wherein the step of installing a collar is performed before the steps of coupling a guide device.

25. A system for fixing a bone, comprising: (A) a guide device including a stem for placement into a medullary canal of a bone and a stop structure adjacent the stem that restricts advancement of the stem into the medullary canal, the guide device also including an external portion connected to the stem and configured, with the stem disposed in the medullary canal, to guide formation of a hole along a transverse path that extends across the bone and that intersects the medullary canal; and (B) an implant including a fastener for placement into the hole and a rod for placement into the medullary canal after removal of the stem, such that the fastener and the rod are disposed in threaded engagement with each other and at least a portion of the bone is compressed longitudinally.

Example 6

Selected Embodiments II—Holder

This example describes selected embodiments of the present disclosure, presented as a series of indexed paragraphs. In particular, this example describes bone fixation apparatus that include a holder for a fastener, and methods of bone fixation that use a holder for positioning a fastener.

1. A system for bone fixation, comprising: (A) an orthopedic device including (i) a rod for placement longitudinally into a medullary canal of a bone, and (ii) a fastener for placement into a transverse hole in the bone that intersects the medullary canal, the fastener defining a long axis and an aperture that receives a portion of the rod such that the rod engages the fastener to lock the rod to the fastener; and (B) a holder device to facilitate installation of the orthopedic device, the holder device being configured to be attached to the fastener such that the holder device and the fastener pivot together about the long axis of the fastener, the holder device including a body and an orientation indicator that, when the holder device is attached to the fastener, extends from the body in a direction corresponding to a pivotal orientation of the aperture about the long axis.

2. The system of paragraph 1, wherein the orientation indicator extends generally radially from the long axis when the holder device is attached to the fastener.

3. The system of paragraph 1, wherein the fastener includes a head and a shank extending from the head, wherein the head has an outer surface spaced from the shank and an inner surface disposed adjacent the shank, and wherein the holder device attaches to the head of the fastener from the outer surface such that the inner surface is not obstructed substantially by the holder device for placement adjacent bone.

4. The system of paragraph 1, wherein the fastener includes a head, and wherein the holder device receives the head in one or more predefined orientations of the fastener relative to the holder device.

5. The system of paragraph 1, wherein the body has opposing ends, and wherein the fastener couples to the holder device and the orientation indicator extends from the body at spaced positions and/or near respective opposing ends of the body.

6. The system of paragraph 1, wherein the holder device is configured to attach to the fastener by threaded engagement with the fastener.

7. A method of fixing a bone, comprising: (A) attaching a fastener to a holder including a body and an orientation indicator such that the orientation indicator extends from the body in a direction corresponding to an orientation of an aperture of the fastener; (B) disposing the fastener transversely in a bone such that the aperture of the fastener is positioned in a medullary canal of the bone; (C) orienting the aperture of the fastener with respect to the medullary canal by aligning the orientation indicator with the bone; and (D) placing a rod into the aperture after the step of orienting such that the rod locks to the fastener and extends longitudinally along the medullary canal.

8. The method of paragraph 7, wherein the step of attaching includes a step of attaching a fastener to a holder having a body and an orientation indicator projecting generally radially from the body.

9. The method of paragraph 7, wherein the step of attaching includes a step of attaching a fastener to a holder having a body with opposing ends such that the fastener is coupled to the holder adjacent an opposing end of the body and such that the orientation indicator projects from the body closer to the other opposing end of the body.

10. The method of paragraph 7, wherein the step of attaching includes a step of disposing the holder in threaded engagement with the fastener.

11. The method of paragraph 7, wherein the step of orienting is performed after the step of disposing.

12. The method of paragraph 7, wherein the step of placing a rod into the aperture includes a step of disposing the rod in threaded engagement with the fastener.

13. The method of paragraph 7, wherein the fastener has a head including a leading exterior surface region and a trailing exterior surface region, wherein the step of attaching substantially exclusively engages the fastener via the trailing exterior surface region relative to the leading exterior surface region.

14. The method of paragraph 7, wherein the step of orienting includes a step of pivoting the holder about a long axis of the fastener while the orientation indicator is engaged by hand.

Example 7

Selected Embodiments III—Collar

This example describes selected embodiments of the present disclosure, presented as a series of indexed paragraphs. In particular, this example describes bone fixation apparatus that include a rod, a fastener, and a collar, and methods of using a fixation apparatus including a rod, a fastener, and a collar to fix bone.

1. A system for bone fixation, comprising: a fixation device including (i) a rod for placement longitudinally into a medullary canal of a bone, the rod including a head opposing a leading end of the rod, (ii) a fastener for placement into a transverse hole in the bone that intersects the medullary canal, the fastener defining an aperture that receives a portion of the rod such that the rod engages the fastener to lock the rod to the fastener, and (iii) a collar having an external thread for threaded engagement with the bone and defining an opening sized to receive the rod from the leading end and to permit advancement of the rod through the collar until the head engages the collar to restrict further advancement of the rod through the collar.

2. The system of paragraph 1, wherein the collar is configured to be disposed at least mostly in the bone.

3. The system of paragraph 1, wherein the collar has a leading end and a trailing end, and wherein the collar defines a helical groove forming at least a portion of the external thread and having a depth that decreases toward the trailing end.

4. The system of paragraph 1, wherein the collar has a leading end and a trailing end, wherein the collar defines a through-hole, and wherein a portion of the through-hole near the trailing end of the collar is relatively larger in diameter to form a countersink for receiving at least a portion of the head of the rod.

5. The system of paragraph 1, further comprising a tool including a first portion for forming a hole in the bone that receives the collar and a second portion for driving the collar into the hole in the bone.

6. A method of fixing bone, comprising: (A) disposing a fastener transversely in a bone such that an aperture of the fastener intersects a medullary canal of the bone; (B) placing a collar into threaded engagement with an end region of the bone; and (C) advancing a rod through the collar and longitudinally in the medullary canal such that a portion of the rod enters the aperture and engages the fastener to lock the rod to the fastener and such that a head of the rod engages the collar to restrict further advancement of the rod into the bone.

7. The method of paragraph 6, further comprising a step of forming a cavity in the bone for receiving the collar, wherein the step of placing a collar includes a step of driving the collar, and wherein the step of forming a cavity and the step of driving the collar are performed using distinct portions of the same tool.

Example 8

Selected Embodiments IV—Rod

This example describes selected embodiments of the present disclosure, presented as a series of indexed paragraphs. In particular, this example describes bone fixation devices that include a rod received by a fastener, and methods of using a rod received by a fastener to fix bone.

1. A device for bone fixation, comprising: (A) a rod for placement longitudinally into the medullary canal, the rod having a body including a trailing section having an external thread for threaded engagement with the internal thread of the fastener and also including a leading section that is smaller in diameter than the external thread and that extends from a forward boundary of the external thread to a leading end of the rod, wherein the leading section includes an elongate tip portion and an intermediate portion disposed between the tip portion and the external thread, and wherein the intermediate portion flares one or more times as the intermediate portion extends toward the external thread; and (B) a fastener for placement into a transverse hole in the bone that intersects the medullary canal, the fastener defining an aperture that receives a portion of the rod such that the rod engages the fastener to lock the rod to the fastener via the external thread.

2. The device of paragraph 1, wherein the leading section includes at least two generally cylindrical segments of distinct diameter.

3. The device of paragraph 2, wherein the at least two generally cylindrical segments of distinct diameter include a forward region and a rearward region and wherein the rearward region is longer than the forward region.

4. The device of paragraph 1, wherein the rod includes a head connected to the body.

5. The device of paragraph 1, wherein the external thread is disposed along less than about one-half the length of the rod.

6. The device of paragraph 1, wherein the external thread defines a threaded region of the rod, and wherein the length of the leading section is at least about one-half the length of the threaded region.

7. The device of paragraph 1, wherein the external thread is formed on a root portion of the rod, and wherein the root portion tapers forward of a leading boundary of the external thread.

8. The device of paragraph 1, wherein the intermediate portion includes a segment that is generally cylindrical.

9. The device of paragraph 1, wherein the rod includes a head connected to the body, and wherein at least a portion of the trailing section between the head and the external thread has a diameter that is substantially greater than the major diameter of the external thread.

10. The device of paragraph 1, wherein the rod includes a head connected to the body, and wherein the length of the trailing section between the head and the external thread is at least about as great as the length of a threaded region of the rod defined by the external thread.

11. A device for bone fixation, comprising: (A) a substantially inflexible rod for placement longitudinally into a medullary canal of a bone; and (B) a fastener for placement into a transverse hole in the bone that intersects the medullary canal, the fastener defining an aperture that receives a portion of the rod such that the rod engages the fastener to lock the rod to the fastener.

12. The device of paragraph 11, wherein the rod has an external thread for threaded engagement with the fastener to lock the rod to the fastener.

13. A device for bone fixation, comprising: (A) a rod for placement longitudinally into a medullary canal of a bone and including a trailing section having a threaded region with an external thread and also including a leading section that is narrower than the threaded region and that extends from a forward boundary of the threaded section to a leading end of the rod; and (B) a fastener including a shaft for transverse placement into the bone and overlapping the medullary canal, the shaft defining an aperture with an internal thread for threaded engagement with the external thread of the threaded region, wherein the length of the leading section is much greater than the diameter of the shaft such that a leading end of the leading section can be advanced through the aperture and then advanced past the shaft by a distance that is greater than the diameter of the shaft.

14. A device for bone fixation, comprising: (A) a fastener for transverse placement into a medullary canal of a bone, the fastener including a shank having a diameter and defining an aperture, the aperture extending crosswise through the shank and including an internal thread; and (B) a rod for longitudinal placement into the medullary canal of the bone, the rod including leading and trailing ends, a head disposed near the trailing end to restrict entry of the rod into bone, and a body extending to the leading end from the head, the body including a threaded region with an external thread structured for threaded engagement with the internal thread of the fastener and also including a leading section extending from a leading boundary of the threaded region to the leading end, the leading section being configured to enter and slide translationally through the aperture over a distance that is much greater than the diameter of the shank, thereby providing a readily noticeable advancement of the rod into bone that indicates proper positioning of the rod for rotational advancement of the threaded region into the aperture and resulting compression of a region of the bone.

15. The device of paragraph 14, wherein the leading section of the body has a length that is at least twice the diameter of the shank of the fastener.

16. The device of paragraph 14, wherein the leading section has a tip portion, and wherein the leading section is structured to center itself in the aperture as the leading section slides translationally through the aperture, if the tip portion enters the aperture off-center.

17. The device of paragraph 14, wherein the leading section has a tip portion near the leading end, and wherein the leading section flares at one or more positions along the leading section as the leading section extends from a trailing border of the tip portion to a leading border of the threaded region.

18. The device of paragraph 14, wherein the leading section of the body tapers in two or more discrete positions along the leading section as the leading section extends from the threaded region to the leading end.

19. The device of paragraph 14, wherein the leading section of the body includes an elongate tip portion with a substantially cylindrical segment, and wherein the leading section tapers in one or more positions as the leading section extends from the threaded region to the cylindrical segment of the tip portion.

20. The device of paragraph 19, wherein the leading section tapers in at least two discrete positions as the leading section extends from the threaded region to the cylindrical segment of the tip portion.

21. The device of paragraph 14, wherein the leading section of the body includes at least two substantially cylindrical segments of different diameter.

22. The device of paragraph 14, wherein the body includes a tail region disposed between the head and the threaded region, and wherein the tail region is wider than the threaded region.

23. The device of paragraph 14, wherein the fastener includes a leading end and a trailing end, and wherein the shank tapers selectively near the leading end of the fastener.

24. A method of fixing a bone, comprising: (A) disposing a fastener transversely in a bone such that an internally threaded aperture of the fastener is positioned in a medullary canal of the bone; (B) advancing a rod longitudinally into the medullary canal such that a leading end of the rod passes through the aperture and then travels past the aperture by a distance greater than a length through the aperture; and (C) rotating the rod into threaded engagement with the aperture of the fastener after the step of advancing.

25. The method of paragraph 24, wherein the rod includes a threaded region configured to engage an internal thread of the aperture and also includes a leading section extending forward from a leading boundary of the threaded region to the leading end of the rod, and wherein the step of advancing includes a step of advancing at least one-half of the length of the leading section completely through the aperture before the step of rotating.

26. The method of paragraph 25, wherein the leading section includes an elongate tip and at least one flared region disposed rearward of the elongate tip and flaring toward the threaded region, and wherein the step of advancing includes a step of advancing the at least one flared region at least into the aperture of the fastener before the step of rotating the rod into threaded engagement with the aperture.

27. The method of paragraph 25, wherein the leading section is configured such that a flared region thereof does not advance readily past the fastener if the rod misses the aperture in the medullary canal.

28. The method of paragraph 24, wherein the rod is configured such that advancement of the rod is blocked by engagement of the rod with a wall of the medullary canal if the rod misses the aperture.

29. The method of paragraph 24, wherein the step of rotating includes a step of rotating the rod until at least a portion of the bone is compressed longitudinally.

30. The method of paragraph 29, wherein the steps of disposing, advancing, and rotating result in compression of an olecranon region of an ulna.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of bone fixation, comprising:
    disposing a guide device such that a first portion of the guide device is disposed longitudinally in a medullary canal of a bone and such that a second portion of the guide device is disposed outside the bone and defines a transverse path across the bone and intersecting the medullary canal;
    forming a transverse hole in the bone along the transverse path, the transverse hole being sized to receive a fastener;
    disposing the fastener in the transverse hole;
    placing a rod longitudinally in the medullary canal such that a threaded portion of the rod enters an aperture of the fastener and engages the fastener at the aperture to lock the rod to the fastener; and
    removing the first portion of the guide device from the medullary canal after the step of forming a transverse hole and before the step of placing a rod.

2. The method of claim 1, wherein the step of disposing a guide device includes a step of advancing the first portion of the guide device into the medullary canal until a stop structure of the guide device restricts further advancement of the first portion.

3. The method of claim 1, further comprising a step of measuring a radial dimension of the bone using, at least in part, the guide device.

4. The method of claim 1, further comprising a step of disposing a collar adjacent an end surface of the bone, wherein the rod includes a head, and wherein the step of placing a rod engages the collar with the head such that the bone is compressed between the collar and the fastener.

5. The method of claim 4, wherein the collar includes an external thread, and wherein the step of disposing a collar creates a threaded engagement of the collar with the bone.

6. The method of claim 1, wherein the first portion of the guide device includes a tapered tip formed near a leading end of the first portion, and wherein the step of disposing a guide device includes a step of placing the tapered tip in the medullary canal.

7. A method of bone fixation, comprising:
    disposing a guide device such that a first portion of the guide device is disposed longitudinally in a proximal region of a medullary canal of a fractured ulna and such that a second portion of the guide device is disposed outside the ulna and defines a transverse path across the ulna and intersecting the medullary canal;
    forming a transverse hole in the ulna along the transverse path;
    disposing a fastener with an aperture in the transverse hole; and
    placing a rod longitudinally in the medullary canal such that a head of the rod engages a collar disposed adjacent a proximal end surface of the ulna and such that a portion of the rod is received in the aperture in threaded engagement with the fastener to lock the rod to the fastener, thereby applying compression to an olecranon region of the ulna,
    wherein the step of forming a transverse hole is performed while the rod is completely outside the ulna,
    wherein the first portion of the guide device has opposing leading and trailing ends, and wherein the step of disposing includes a step of disposing the leading end between the transverse path and a proximal end of the ulna.

8. The method of claim 7, wherein the step of disposing a guide device includes a step of advancing the first portion of the guide device into the medullary canal until a stop structure of the guide device restricts further advancement of the first portion.

9. The method of claim 7, further comprising a step of disposing the collar in threaded engagement with the ulna.

10. The method of claim 7, wherein the first portion of the guide device includes a tapered tip formed near a leading end of the first portion, and wherein the step of disposing a guide device includes a step of placing the tapered tip in the medullary canal.

* * * * *